(12) United States Patent
Zhang et al.

(10) Patent No.: US 11,958,813 B2
(45) Date of Patent: Apr. 16, 2024

(54) URACIL COMPOUND CONTAINING CARBOXYLATE FRAGMENT, PREPARATION METHOD THEREFOR, AND HERBICIDAL COMPOSITION AND USE THEREOF

(71) Applicant: JIANGSU FLAG CHEMICAL INDUSTRY CO., LTD., Nanjing (CN)

(72) Inventors: Pu Zhang, Nanjing (CN); Kaicheng Yao, Nanjing (CN); Yaojun Wu, Nanjing (CN); Dan Xu, Nanjing (CN); Pin Qian, Nanjing (CN); Long Bu, Nanjing (CN); Congqiang Bai, Nanjing (CN)

(73) Assignee: JIANGSU FLAG CHEMICAL INDUSTRY CO., LTD., Nanjing (CN)

( * ) Notice: Subject to any disclaimer, the term of this patent is extended or adjusted under 35 U.S.C. 154(b) by 0 days.

(21) Appl. No.: 18/276,036

(22) PCT Filed: Feb. 5, 2022

(86) PCT No.: PCT/CN2022/075322
§ 371 (c)(1),
(2) Date: Aug. 6, 2023

(87) PCT Pub. No.: WO2022/166938
PCT Pub. Date: Aug. 11, 2022

(65) Prior Publication Data
US 2024/0059660 A1 Feb. 22, 2024

(30) Foreign Application Priority Data

Feb. 7, 2021 (CN) .......................... 202110167827.1

(51) Int. Cl.
*C07D 239/10* (2006.01)
*A01N 43/54* (2006.01)
*A01P 13/00* (2006.01)
*C07D 405/12* (2006.01)

(52) U.S. Cl.
CPC ........... *C07D 239/10* (2013.01); *A01N 43/54* (2013.01); *A01P 13/00* (2021.08); *C07D 405/12* (2013.01)

(58) Field of Classification Search
None
See application file for complete search history.

(56) References Cited

U.S. PATENT DOCUMENTS 5,183,492 A 2/1993 Suchy et al.

FOREIGN PATENT DOCUMENTS

| CN | 1325624 A | 12/2001 |
|---|---|---|
| DE | 19741411 A1 | 3/1998 |
| EP | 0831091 A2 | 3/1998 |

*Primary Examiner* — Alton N Pryor
(74) *Attorney, Agent, or Firm* — Bayramoglu Law Offices LLC

(57) ABSTRACT

A uracil compound containing a carboxylate fragment, a preparation method therefor, and a herbicidal composition and use thereof are provided. The preparation method includes a contact reaction between a carboxylic acid compound and different substituted alcohol, halogenated, or sulfonate compound in a presence of a solvent. The uracil compound containing a carboxylate fragment provided by the present invention has better herbicidal activity compared with the prior art.

16 Claims, No Drawings

URACIL COMPOUND CONTAINING CARBOXYLATE FRAGMENT, PREPARATION METHOD THEREFOR, AND HERBICIDAL COMPOSITION AND USE THEREOF

CROSS REFERENCE TO THE RELATED APPLICATIONS

This application is the national phase entry of International Application No. PCT/CN2022/075322, filed on Feb. 5, 2022, which is based upon and claims priority to Chinese Patent Application No. 202110167827.1, filed on Feb. 7, 2021, the entire contents of which are incorporated herein by reference.

TECHNICAL FIELD

The present invention relates to the field of pesticide herbicides, and in particular, to a uracil compound containing a carboxylate fragment, a preparation method therefor, and a herbicidal composition and use thereof.

BACKGROUND

Chemical weed control with herbicides is the most economical and effective means of weed control. However, long-term and continuous use of single varieties or singles mode of action of chemical herbicides in high doses easily lead to problems such as weed resistance and resistance evolution. Development of new varieties of pesticides is a core means to solve the problems.

Protoporphyrinogen oxidase (PPO, EC 1.3.3.4) can catalyze oxidation of protoporphyrinogen IX into protoporphyrin IX. The PPO is a key enzyme in the same biosynthetic step of chlorophyll and heme. Inhibiting PPO in plants ultimately leads to accumulation and leakage of substrate protoporphyrin IX into cytoplasm, causing lipid peroxidation of the cytoplasm and albinism and death of the plants. In the past few decades, PPO has been widely studied as an important herbicide target.

Studies on uracil compounds as herbicides began in the 1960s and reached a peak in the 1990s. In recent years, few varieties have been developed, and patents reported uracil compounds sometimes. For example, CIBA-GEIGY Company disclosed a structure of the following general formula in U.S. Pat. No. 5,183,492A:

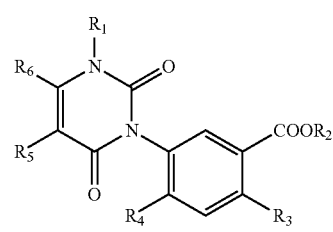

After that, Syngenta successfully developed a commercial herbicide Butafenacil (compound 47 in U.S. Pat. No. 5,183,492A), which is mainly used in orchards, including vineyards, cotton fields, and non-cultivated lands to control important gramineous weeds, broad-leaved weeds, sedges, and the like, with good weed control effects.

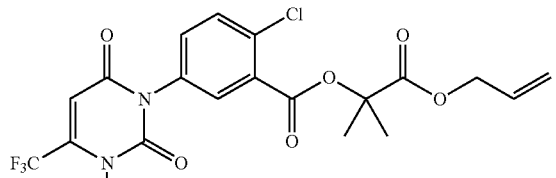

Butafenacil

U.S. Pat. No. 5,183,492A also disclosed preparation of benzoyloxy propionate CK (compound 1 in the application) as follows:

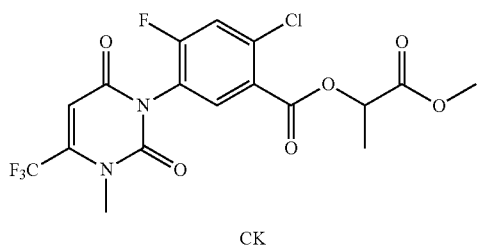 [SMILES: COC(=O)C(C)OC(=O)c1cc(-n2c(=O)cc(C(F)(F)F)n(C)c2=O)c(F)cc1Cl ; "CK"]

CK

In summary, existing uracil compound herbicides are relatively single in varieties, with little choice. Therefore, novel uracil herbicides with good herbicidal activity are urgently needed in the market.

SUMMARY

A technical problem to be solved by the present invention is to provide a novel uracil herbicide with good herbicidal activity.

A technical solution for the present invention to solve the above technical problem is as follows:

A uracil compound containing a carboxylate fragment, a structure of which is shown in the following general formula (I):

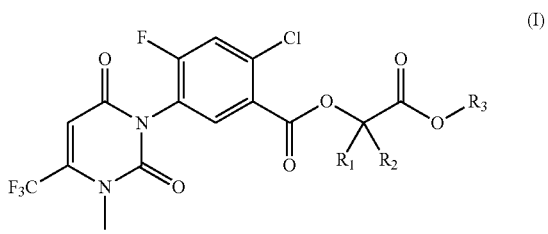

the formula:
$R_1$ and $R_2$ are selected from hydrogen or methyl respectively; or $R_1$ and $R_2$ together with the carbon atom they are attached form a 3-membered carbocycle;
$R_3$ is selected from $C_{1-3}$ alkoxy $C_{1-3}$ alkyl, $C_{1-3}$ haloalkoxy $C_{1-3}$ alkyl, $C_{2-6}$ alkenoxy $C_{1-3}$ alkyl, $C_{2-6}$ haloalkenoxy $C_{1-3}$ alkyl, $C_{2-6}$ alkynoxy $C_{1-3}$ alkyl, $C_{2-6}$ haloalkynoxy $C_{1-3}$ alkyl, $C_{1-3}$ alkyl $S(O)_n$ $C_{1-3}$ alkyl, $C_{3-6}$ oxygen-containing cycloalkyl $C_{1-3}$ alkyl, or $C_{3-9}$ oxygen-containing cycloalkyl;
n=0, 1, or 2; and
when $R_1$ is selected from hydrogen and $R_2$ is selected from methyl, the chiral carbon atom connected thereto may be selected from either an R configuration or an S configuration, or a mixture of the two.

According to a preferred compound of the present invention, in the general formula (I):
- $R_1$ and $R_2$ are selected from hydrogen or methyl respectively; or $R_1$ and $R_2$ together with the carbon atom they are attached form a 3-membered carbocycle;
- $R_3$ is selected from $C_{1-3}$ alkoxy $C_{1-3}$ alkyl, $C_{1-3}$ haloalkoxy $C_{1-3}$ alkyl, $C_{2-6}$ alkenoxy $C_{1-3}$ alkyl, $C_{2-6}$ haloalkenoxy $C_{1-3}$ alkyl, $C_{2-6}$ alkynoxy $C_{1-3}$ alkyl, $C_{2-6}$ haloalkynoxy $C_{1-3}$ alkyl, $C_{3-6}$ oxygen-containing cycloalkyl $C_{1-3}$ alkyl, or $C_{3-9}$ oxygen-containing cycloalkyl; and
- when $R_1$ is selected from hydrogen and $R_2$ is selected from methyl, the chiral carbon atom connected thereto may be selected from either an R configuration or an S configuration, or a mixture of the two; and in the mixture, a ratio of R to S is 1:99 to 99:1.

According to a more preferred compound of the present invention, in the general formula (I):
- $R_1$ and $R_2$ are selected from hydrogen or methyl respectively;
- $R_3$ is selected from $C_{1-3}$ alkoxy $C_{1-3}$ alkyl, $C_{1-3}$ haloalkoxy $C_{1-3}$ alkyl, $C_{2-6}$ alkenoxy $C_{1-3}$ alkyl, $C_{2-6}$ haloalkenoxy $C_{1-3}$ alkyl, $C_{2-6}$ alkynoxy $C_{1-3}$ alkyl, $C_{2-6}$ haloalkynoxy $C_{1-3}$ alkyl, $C_{3-6}$ oxygen-containing cycloalkyl $C_{1-3}$ alkyl, or $C_{3-9}$ oxygen-containing cycloalkyl; and
- when $R_1$ is selected from hydrogen and $R_2$ is selected from methyl, the chiral carbon atom connected thereto may be selected from either an R configuration or an S configuration, or a mixture of the two; and in the mixture, a ratio of R to S is 1:99 to 99:1.

In definitions of the compounds of the general formula (I) given above, the used terms are generally defined as follows:

Halogen: fluorine, chlorine, bromine, or iodine. Alkyl: linear or branched alkyl, such as methyl, ethyl, propyl, isopropyl, n-butyl, tertiary or secondary butyl, and isomers. Alkenyl: linear or branched alkenes, such as vinyl, 1-propenyl, 2-propenyl, and different butenyl, pentenyl and hexenyl isomers. The alkenyl further includes polyenes, such as 1,2-prodienyl and 2,4-hexadienyl. Alkynyl: linear or branched alkynes, such as ethynyl, propynyl, and different butynyl, pentynyl and hexynyl isomers. The alkynyl further includes polyynes, such as 2,4-hexanediynyl. Alkoxyalkyl: alkyl-O-alkyl-, such as $CH_3OCH_2$—. Haloalkoxyalkyl: alkyl-on which hydrogen atoms may be partially or completely substituted by halogen atoms, such as $C_1CH_2OCH_2$—. Alkenoxy: alkenyl-O-alkyl-, such as $CH_2=CHCH_2OCH_2CH_2$—. Haloalkenoxyalkyl: alkenyl-O-alkyl, where O and $CH_2=CH$ are not directly connected, and hydrogen atoms on the alkenyls may be partially or completely substituted by halogen atoms, such as $ClCH=CHCH_2OCH_2CH_2$—. Alkynoxyalkyl: alkynyl-O-alkyl-, such as $CH\equiv CCH_2OCH_2CH_2$—, where O and CHC are not directly connected. Haloalkynoxyalkyl: alkynyl-O-alkyl-, where hydrogen atoms on the alkynyls may be substituted by halogen atoms, such as $ClCCCH_2OCH_2CH_2$—. Alkyl $S(O)_n$ alkyl: alkyl-$S(O)_n$-alkyl-, n=0, 1 or 2, such as $CH_3SCH_2CH_2$—, $CH_3SOCH_2CH_2$—, and $CH_3SO_2CH_2CH_2$—. Oxygen-containing cycloalkyl: substituted or unsubstituted cyclic oxygen-containing alkyl, such as

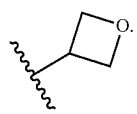

Substituent groups include methyl, halogen, cyano, and the like. Oxygen-containing-cycloalkyl-alkyl: substituted or unsubstituted alkyl with cyclic oxygen-containing alkyl, such as

where substituent groups include methyl, halogen, cyano, and the like.

Some compounds of the present invention may be described by using specific compounds listed in Table 1, but the present invention is not limited to these compounds.

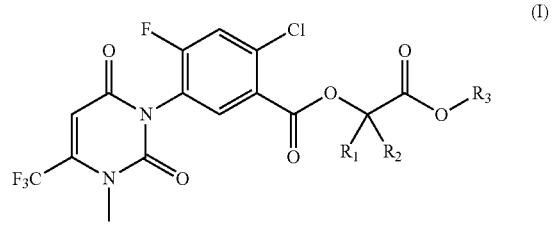

(I)

TABLE 2

| Number of compound | $R_1$ | $R_2$ | $R_3$ | State | Melting point |
|---|---|---|---|---|---|
| 1 | H | H | ![methoxymethyl] | | |
| 2 | H | H | ![ethoxymethyl] | | |
| 3 | H | H | ![methoxyethyl] | Colorless oil | — |

TABLE 2-continued
| Number of compound | R$_1$ | R$_2$ | R$_3$ | State | Melting point |
|---|---|---|---|---|---|
| 4 | H | H | 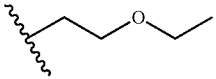 | | |
| 5 | H | H | 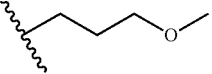 | | |
| 6 | H | H | 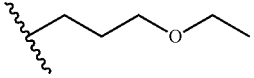 [SMILES: *CCCOCC] | | |
| 7 | H | H | 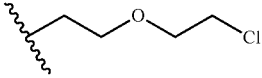 [SMILES: *CCOCCCl] | | |
| 8 | H | H | 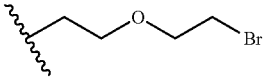 [SMILES: *CCOCCBr] | | |
| 9 | H | H | 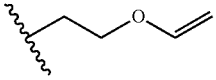 [SMILES: *CCOC=C] | | |
| 10 | H | H | 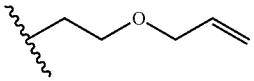 [SMILES: *CCOCC=C] | Light yellow oil | — |
| 11 | H | H | 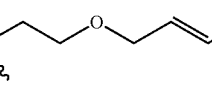 | | |
| 12 | H | H | 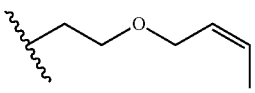 [SMILES: *CCOC/C=C\C] | | |
| 13 | H | H | 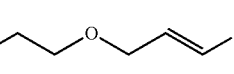 | | |
| 14 | H | H | 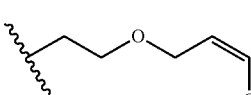 | | |
| 15 | H | H | 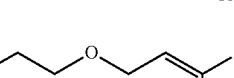 | | |
| 16 | H | H |  | | |
| 17 | H | H | 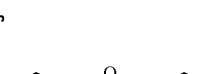 | | |
| 18 | H | H |  | | |

TABLE 2-continued
| Number of compound | R$_1$ | R$_2$ | R$_3$ | State | Melting point |
|---|---|---|---|---|---|
| 19 | H | H | 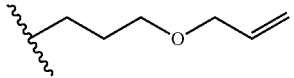 [SMILES: *CCCOCC=C] | | |
| 20 | H | H | 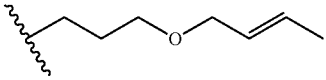 [SMILES: *CCCOC/C=C/C] | | |
| 21 | H | H | 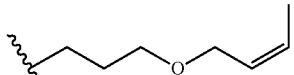 | | |
| 22 | H | H | 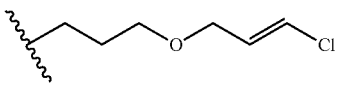 [SMILES: *CCCOC/C=C/Cl] | | |
| 23 | H | H | 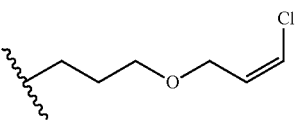 [SMILES: *CCCOC/C=C\Cl] | | |
| 24 | H | H | 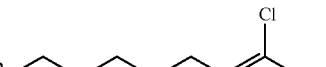 | | |
| 25 | H | H | 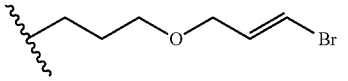 [SMILES: *CCCOC/C=C/Br] | | |
| 26 | H | H | 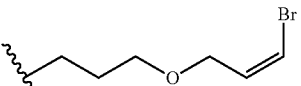 | | |
| 27 | H | H | 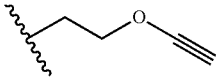 [SMILES: *CCOC#C] | | |
| 28 | H | H | 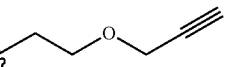 | Light yellow oil | — |
| 29 | H | H | 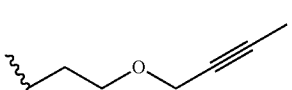 | | |
| 30 | H | H | 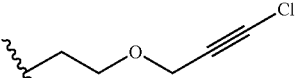 | | |
| 31 | H | H | 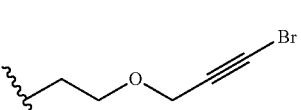 | | |

TABLE 2-continued
| Number of compound | R$_1$ | R$_2$ | R$_3$ | State | Melting point |
|---|---|---|---|---|---|
| 32 | H | H | 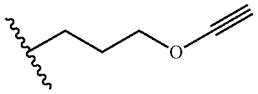 [SMILES: *CCCOC#C] | | |
| 33 | H | H | 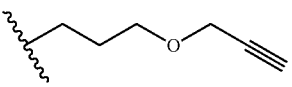 [SMILES: *CCCOCC#C] | | |
| 34 | H | H | 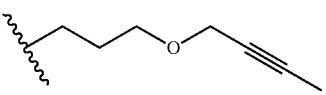 [SMILES: *CCCOCC#CC] | | |
| 35 | H | H | 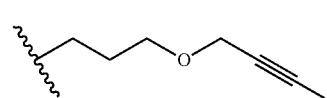 | | |
| 36 | H | H | 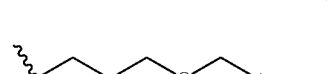 | | |
| 37 | H | H | 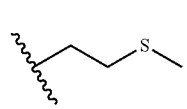 | | |
| 38 | H | H | 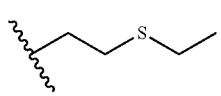 | | |
| 39 | H | H | 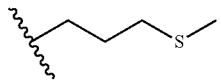 [SMILES: *CCCSC] | | |
| 40 | H | H | 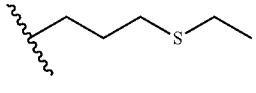 | | |
| 41 | H | H | 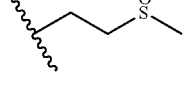 | | |
| 42 | H | H | 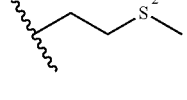 | | |
| 43 | H | H | 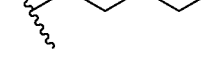 | | |
| 44 | H | H | 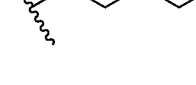 | | |
| 45 | H | H |  | | |

TABLE 2-continued
| Number of compound | R₁ | R₂ | R₃ | State | Melting point |
|---|---|---|---|---|---|
| 46 | H | H | 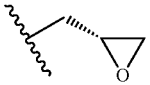 | | |
| 47 | H | H | 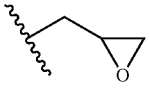 | | |
| 48 | H | H | 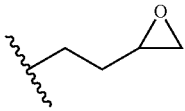 | | |
| 49 | H | H | 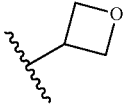 | | |
| 50 | H | H | 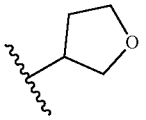 | | |
| 51 | H | H | 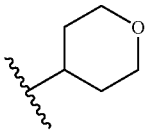 | | |
| 52 | H |  | 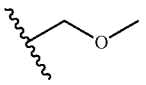 | | |
| 53 | H |  | 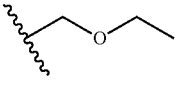 [SMILES: *COCC] | | |
| 54 | H |  | 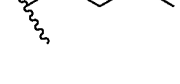 | Colorless oil | — |
| 55 | H |  | 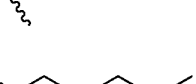 | | |
| 56 | H |  | 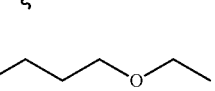 | | |
| 57 | H |  | 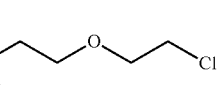 | | |
| 58 | H |  | 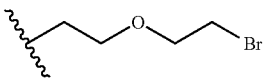 [SMILES: *CCOCCBr] | | |
| 59 | H |  |  | | |

TABLE 2-continued
| Number of compound | R₁ | R₂ | R₃ | State | Melting point |
|---|---|---|---|---|---|
| 60 | H |  | 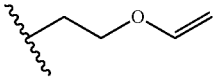 [SMILES: *CCOC=C] | | |
| 61 | H |  | 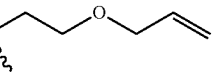 | Colorless oil | — |
| 62 | H |  | 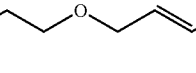 | | |
| 63 | H |  | 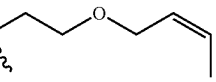 | | |
| 64 | H |  | 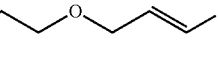 | | |
| 65 | H |  | 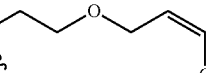 | | |
| 66 | H |  | 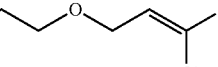 | | |
| 67 | H |  | 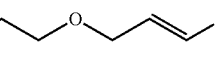 | | |
| 68 | H |  | 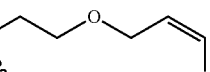 | | |
| 69 | H |  | 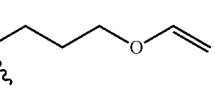 | | |
| 70 | H |  | 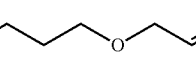 | | |
| 71 | H |  | 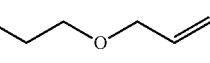 | | |
| 72 | H |  | 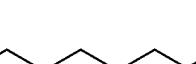 | | |
| 73 | H |  | 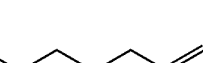 | | |
| 74 | H |  |  | | |

TABLE 2-continued

| Number of compound | R₁ | R₂ | R₃ | State | Melting point |
|---|---|---|---|---|---|
| 75 | H | -CH(CH₃)- | -(CH₂)₃-O-CH₂-CH=CCl₂ | | |
| 76 | H | -CH(CH₃)- | -(CH₂)₃-O-CH₂-CH=CH-Br (E) | | |
| 77 | H | -CH(CH₃)- | -(CH₂)₃-O-CH₂-CH=CH-Br (Z) | | |
| 78 | H | -CH(CH₃)- | -(CH₂)₂-O-C≡CH | | |
| 79 | H | -CH(CH₃)- | -(CH₂)₂-O-CH₂-C≡CH | Colorless oil | — |
| 80 | H | -CH(CH₃)- | -(CH₂)₂-O-CH₂-C≡C-CH₃ | | |
| 81 | H | -CH(CH₃)- | -(CH₂)₂-O-CH₂-C≡C-Cl | | |
| 82 | H | -CH(CH₃)- | -(CH₂)₂-O-CH₂-C≡C-Br | | |
| 83 | H | -CH(CH₃)- | -(CH₂)₃-O-C≡CH | | |
| 84 | H | -CH(CH₃)- | -(CH₂)₃-O-CH₂-C≡CH | | |
| 85 | H | -CH(CH₃)- | -(CH₂)₃-O-CH₂-C≡C-CH₃ | | |
| 86 | H | -CH(CH₃)- | -(CH₂)₃-O-CH₂-C≡C-Cl | | |
| 87 | H | -CH(CH₃)- | -(CH₂)₃-O-CH₂-C≡C-Br | | |
| 88 | H | -CH(CH₃)- | -(CH₂)₂-S-CH₃ | Colorless oil | — |

TABLE 2-continued

| Number of compound | R₁ | R₂ | R₃ | State | Melting point |
|---|---|---|---|---|---|
| 89 | H | –CH₃ | –CH₂CH₂–S–CH₂CH₃ | | |
| 90 | H | –CH₃ | –CH₂CH₂CH₂–S–CH₃ | | |
| 91 | H | –CH₃ | –CH₂CH₂CH₂–S–CH₂CH₃ | | |
| 92 | H | –CH₃ | –CH₂CH₂–S(O)–CH₃ | Colorless oil | — |
| 93 | H | –CH₃ | –CH₂CH₂–S(O)₂–CH₃ | Colorless oil | — |
| 94 | H | –CH₃ | –CH₂CH₂–S(O)–CH₂CH₃ | | |
| 95 | H | –CH₃ | –CH₂CH₂–S(O)₂–CH₂CH₃ | | |
| 96 | H | –CH₃ | –CH₂-(epoxide) | Colorless oil | — |
| 97 | H | –CH₃ | –CH₂-(epoxide, stereo) | Colorless oil | — |
| 98 | H | –CH₃ | –CH₂-(epoxide) | | |
| 99 | H | –CH₃ | –CH₂CH₂CH₂-(epoxide) | | |
| 100 | H | –CH₃ | oxetan-3-yl | | |
| 101 | H | –CH₃ | tetrahydrofuran-3-yl | | |
| 102 | H | –CH₃ | tetrahydropyran-4-yl | | |

TABLE 2-continued
| Number of compound | R₁ | R₂ | R₃ | State | Melting point |
|---|---|---|---|---|---|
| 103 | H |  | 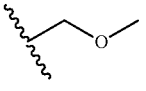 [SMILES: *COC] | | |
| 104 | H |  | 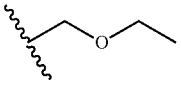 [SMILES: *COCC] | | |
| 105 | H |  | 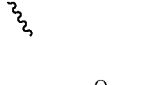 | Colorless oil | — |
| 106 | H |  | 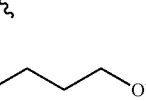 | | |
| 107 | H |  | 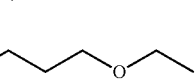 | | |
| 108 | H |  | 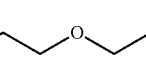 | | |
| 109 | H |  | 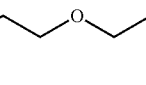 | | |
| 110 | H |  | 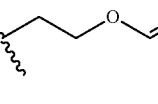 | | |
| 111 | H |  |  | | |
| 112 | H |  | 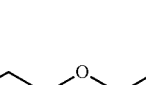 | Colorless oil | — |
| 113 | H |  | 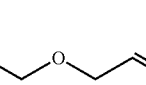 | | |
| 114 | H |  | 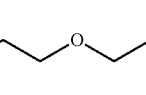 | | |
| 115 | H |  | 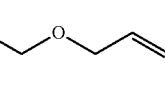 | | |
| 116 | H |  |  | | |
| 117 | H | | | | |

TABLE 2-continued

| Number of compound | R₁ | R₂ | R₃ | State | Melting point |
|---|---|---|---|---|---|
| 118 | H | •••CH₃ | ~~~O~~~Br (E) | | |
| 119 | H | •••CH₃ | ~~~O~~~Br (Z) | | |
| 120 | H | •••CH₃ | ~~~O-vinyl | | |
| 121 | H | •••CH₃ | ~~~O-allyl | | |
| 122 | H | •••CH₃ | ~~~O-CH=CH-CH₃ (E) | | |
| 123 | H | •••CH₃ | ~~~O-CH=CH-CH₃ (Z) | | |
| 124 | H | •••CH₃ | ~~~O~~~Cl (E) | | |
| 125 | H | •••CH₃ | ~~~O~~~Cl (Z) | | |
| 126 | H | •••CH₃ | ~~~O-CH=CCl₂ | | |
| 127 | H | •••CH₃ | ~~~O~~~Br (E) | | |
| 128 | H | •••CH₃ | ~~~O~~~Br (Z) | | |
| 129 | H | •••CH₃ | ~~~O-C≡CH | | |
| 130 | H | •••CH₃ | ~~~O-CH₂-C≡CH | Colorless oil | — |
| 131 | H | •••CH₃ | ~~~O-CH₂-C≡C-CH₃ | | |

TABLE 2-continued
| Number of compound | R$_1$ | R$_2$ | R$_3$ | State | Melting point |
|---|---|---|---|---|---|
| 132 | H | 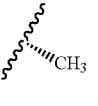 | 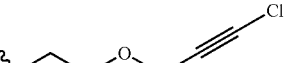 | | |
| 133 | H | 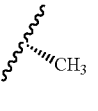 | 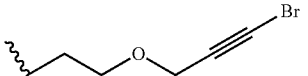 | | |
| 134 | H | 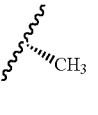 | 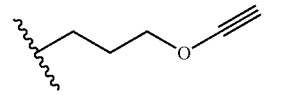 [SMILES: *CCCOC#C] | | |
| 135 | H |  | 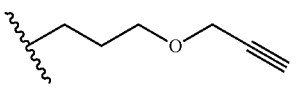 [SMILES: *CCCOCC#C] | | |
| 136 | H | 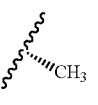 | 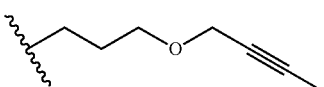 | | |
| 137 | H | 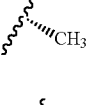 | 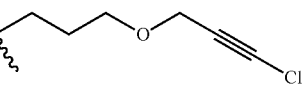 | | |
| 138 | H | 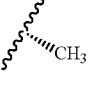 | 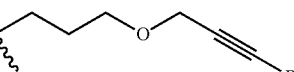 | | |
| 139 | H | 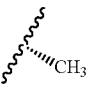 | 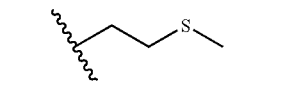 [SMILES: *CCSC] | Colorless oil | — |
| 140 | H | 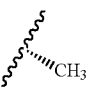 | 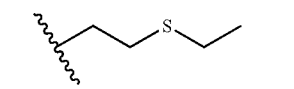 [SMILES: *CCSCC] | | |
| 141 | H | 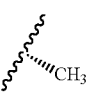 | 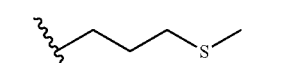 | | |
| 142 | H | 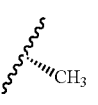 | 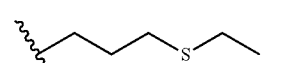 | | |
| 143 | H | 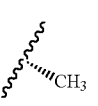 | 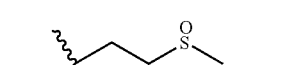 | Colorless oil | — |
| 144 | H | 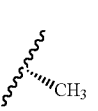 | 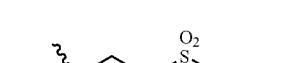 | Colorless oil | — |
| 145 | H |  | 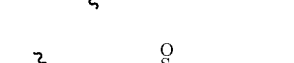 | | |

TABLE 2-continued
| Number of compound | R₁ | R₂ | R₃ | State | Melting point |
|---|---|---|---|---|---|
| 146 | H |  | 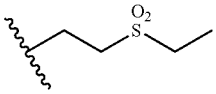 | | |
| 147 | H |  | 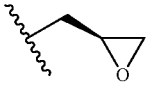 [SMILES: *C[C@H]1CO1] | Colorless oil | — |
| 148 | H |  |  | Colorless oil | — |
| 149 | H |  | 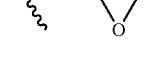 | | |
| 150 | H |  | 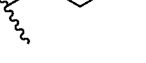 | | |
| 151 | H |  | 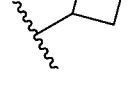 | | |
| 152 | H |  | 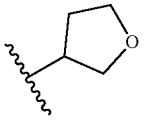 [SMILES: *C1CCOC1] | | |
| 153 | H |  | 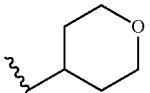 | | |
| 154 | CH₃ | H | 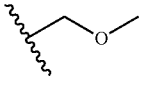 [SMILES: *COC] | | |
| 155 | CH₃ | H | 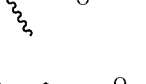 | | |
| 156 | CH₃ | H | 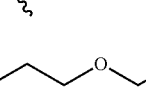 | Colorless oil | — |
| 157 | CH₃ | H | 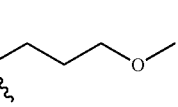 | | |
| 158 | CH₃ | H | 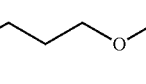 | | |
| 159 | CH₃ | H |  | | |

TABLE 2-continued
| Number of compound | R₁ | R₂ | R₃ | State | Melting point |
|---|---|---|---|---|---|
| 160 | CH₃ | H | 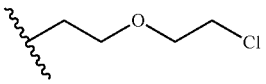 [SMILES: *CCOCCCl] | | |
| 161 | CH₃ | H | 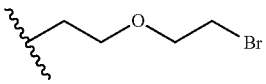 [SMILES: *CCOCCBr] | | |
| 162 | CH₃ | H | 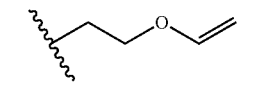 [SMILES: *CCOC=C] | | |
| 163 | CH₃ | H | 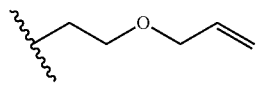 [SMILES: *CCOCC=C] | Colorless oil | — |
| 164 | CH₃ | H | 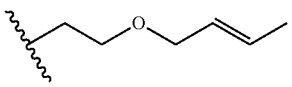 [SMILES: *CCOC/C=C/C] | | |
| 165 | CH₃ | H | 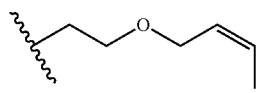 [SMILES: *CCOC/C=C\C] | | |
| 166 | CH₃ | H | 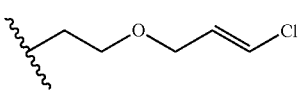 [SMILES: *CCOC/C=C/Cl] | | |
| 167 | CH₃ | H | 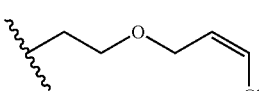 | | |
| 168 | CH₃ | H | 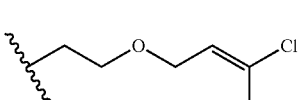 | | |
| 169 | CH₃ | H | 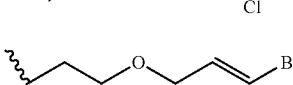 | | |
| 170 | CH₃ | H | 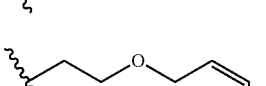 | | |
| 171 | CH₃ | H | 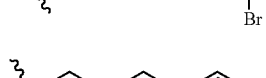 | | |
| 172 | CH₃ | H |  | | |
| 173 | CH₃ | H |  | | |
| 174 | CH₃ | H |  | | |

TABLE 2-continued
| Number of compound | R₁ | R₂ | R₃ | State | Melting point |
|---|---|---|---|---|---|
| 175 | CH₃ | H | 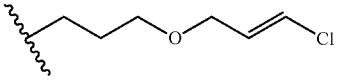 [SMILES: *CCCOC/C=C/Cl] | | |
| 176 | CH₃ | H | 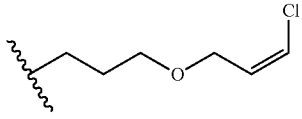 [SMILES: *CCCOC/C=C\Cl] | | |
| 177 | CH₃ | H | 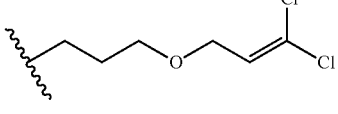 | | |
| 178 | CH₃ | H | 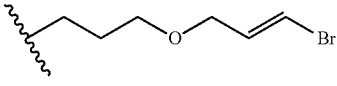 [SMILES: *CCCOC/C=C/Br] | | |
| 179 | CH₃ | H | 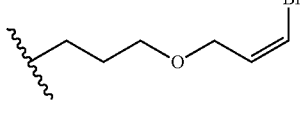 | | |
| 180 | CH₃ | H | 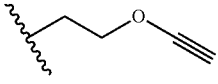 [SMILES: *CCOC#C] | | |
| 181 | CH₃ | H | 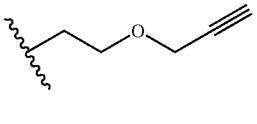 [SMILES: *CCOCC#C] | Colorless oil | — |
| 182 | CH₃ | H | 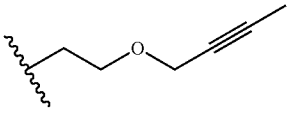 [SMILES: *CCOCC#CC] | | |
| 183 | CH₃ | H | 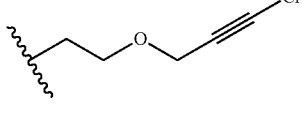 | | |
| 184 | CH₃ | H | 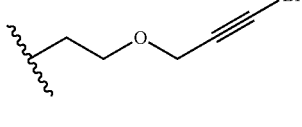 | | |
| 185 | CH₃ | H | 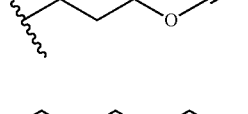 | | |
| 186 | CH₃ | H | 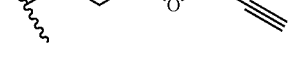 | | |
| 187 | CH₃ | H | 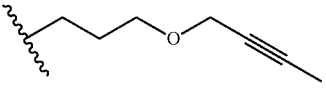 [SMILES: *CCCOCC#CC] | | |

TABLE 2-continued

| Number of compound | R₁ | R₂ | R₃ | State | Melting point |
|---|---|---|---|---|---|
| 188 | CH₃ | H | ~~~~-CH₂CH₂CH₂-O-CH₂-C≡C-Cl | | |
| 189 | CH₃ | H | ~~~~-CH₂CH₂CH₂-O-CH₂-C≡C-Br | | |
| 190 | CH₃ | H | ~~~~-CH₂CH₂-S-CH₃ | Colorless oil | — |
| 191 | CH₃ | H | ~~~~-CH₂CH₂-S-CH₂CH₃ | | |
| 192 | CH₃ | H | ~~~~-CH₂CH₂CH₂-S-CH₃ | | |
| 193 | CH₃ | H | ~~~~-CH₂CH₂CH₂-S-CH₂CH₃ | | |
| 194 | CH₃ | H | ~~~~-CH₂CH₂-S(=O)-CH₃ | Colorless oil | — |
| 195 | CH₃ | H | ~~~~-CH₂CH₂-S(O₂)-CH₃ | Colorless oil | — |
| 196 | CH₃ | H | ~~~~-CH₂CH₂-S(=O)-CH₂CH₃ | | |
| 197 | CH₃ | H | ~~~~-CH₂CH₂-S(O₂)-CH₂CH₃ | | |
| 198 | CH₃ | H | ~~~~-CH₂-(epoxide, wedge) | Colorless oil | — |
| 199 | CH₃ | H | ~~~~-CH₂-(epoxide, dashed) | Colorless oil | — |
| 200 | CH₃ | H | ~~~~-CH₂-(epoxide) | | |
| 201 | CH₃ | H | ~~~~-CH₂CH₂-(epoxide) | | |

TABLE 2-continued

| Number of compound | R₁ | R₂ | R₃ | State | Melting point |
|---|---|---|---|---|---|
| 202 | CH₃ | H | 3-oxetanyl | | |
| 203 | CH₃ | H | tetrahydrofuran-3-yl | | |
| 204 | CH₃ | H | tetrahydropyran-4-yl | | |
| 205 | CH₃ | CH₃ | —CH₂—O—CH₃ | | |
| 206 | CH₃ | CH₃ | —CH₂—O—CH₂CH₃ | | |
| 207 | CH₃ | CH₃ | —CH₂CH₂—O—CH₃ | White solid | 71.5-79.7° C. |
| 208 | CH₃ | CH₃ | —CH₂CH₂—O—CH₂CH₃ | | |
| 209 | CH₃ | CH₃ | —CH₂CH₂CH₂—O—CH₃ | | |
| 210 | CH₃ | CH₃ | —CH₂CH₂CH₂—O—CH₂CH₃ | | |
| 211 | CH₃ | CH₃ | —CH₂CH₂—O—CH₂CH₂Cl | | |
| 212 | CH₃ | CH₃ | —CH₂CH₂—O—CH₂CH₂Br | | |
| 213 | CH₃ | CH₃ | —CH₂CH₂—O—CH=CH₂ | | |
| 214 | CH₃ | CH₃ | —CH₂CH₂—O—CH₂CH=CH₂ | Colorless oil | — |
| 215 | CH₃ | CH₃ | —CH₂CH₂—O—CH₂CH=CHCH₃ | | |

TABLE 2-continued

| Number of compound | R₁ | R₂ | R₃ | State | Melting point |
|---|---|---|---|---|---|
| 216 | CH₃ | CH₃ | ~~~CH₂CH₂CH₂-O-CH₂-CH=CH-CH₃ (cis) | | |
| 217 | CH₃ | CH₃ | ~~~CH₂CH₂CH₂-O-CH₂-CH=CH-Cl (trans) | | |
| 218 | CH₃ | CH₃ | ~~~CH₂CH₂CH₂-O-CH₂-CH=CH-Cl (cis) | | |
| 219 | CH₃ | CH₃ | ~~~CH₂CH₂CH₂-O-CH₂-CH=CCl₂ | | |
| 220 | CH₃ | CH₃ | ~~~CH₂CH₂CH₂-O-CH₂-CH=CH-Br (trans) | | |
| 221 | CH₃ | CH₃ | ~~~CH₂CH₂CH₂-O-CH₂-CH=CH-Br (cis) | | |
| 222 | CH₃ | CH₃ | ~~~CH₂CH₂CH₂CH₂-O-CH=CH₂ | | |
| 223 | CH₃ | CH₃ | ~~~CH₂CH₂CH₂CH₂-O-CH₂-CH=CH₂ | | |
| 224 | CH₃ | CH₃ | ~~~CH₂CH₂CH₂CH₂-O-CH₂-CH=CH-CH₃ (trans) | | |
| 225 | CH₃ | CH₃ | ~~~CH₂CH₂CH₂CH₂-O-CH₂-CH=CH-CH₃ (cis) | | |
| 226 | CH₃ | CH₃ | ~~~CH₂CH₂CH₂CH₂-O-CH₂-CH=CH-Cl (trans) | | |
| 227 | CH₃ | CH₃ | ~~~CH₂CH₂CH₂CH₂-O-CH₂-CH=CH-Cl (cis) | | |
| 228 | CH₃ | CH₃ | ~~~CH₂CH₂CH₂CH₂-O-CH₂-CH=CCl₂ | | |
| 229 | CH₃ | CH₃ | ~~~CH₂CH₂CH₂CH₂-O-CH₂-CH=CH-Br (trans) | | |

TABLE 2-continued
| Number of compound | R₁ | R₂ | R₃ | State | Melting point |
|---|---|---|---|---|---|
| 230 | CH₃ | CH₃ | 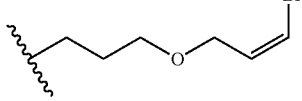 | | |
| 231 | CH₃ | CH₃ | 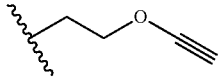 [SMILES: *CCOC#C] | | |
| 232 | CH₃ | CH₃ | 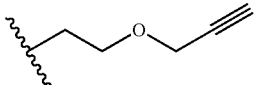 [SMILES: *CCOCC#C] | | |
| 233 | CH₃ | CH₃ | 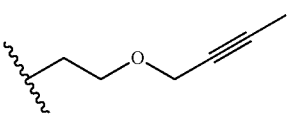 [SMILES: *CCOCC#CC] | | |
| 234 | CH₃ | CH₃ | 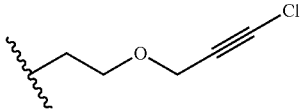 [SMILES: *CCOCC#CCl] | | |
| 235 | CH₃ | CH₃ | 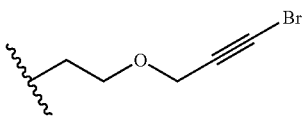 [SMILES: *CCOCC#CBr] | | |
| 236 | CH₃ | CH₃ | 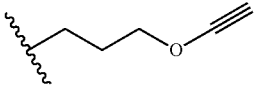 [SMILES: *CCCOC#C] | | |
| 237 | CH₃ | CH₃ | 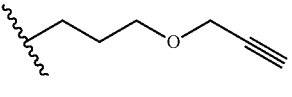 [SMILES: *CCCOCC#C] | | |
| 238 | CH₃ | CH₃ | 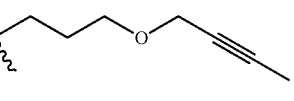 | | |
| 239 | CH₃ | CH₃ | 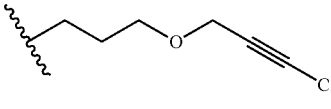 | | |
| 240 | CH₃ | CH₃ | 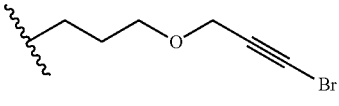 [SMILES: *CCCOCC#CBr] | | |
| 241 | CH₃ | CH₃ | 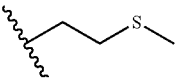 [SMILES: *CCSC] | | |
| 242 | CH₃ | CH₃ | 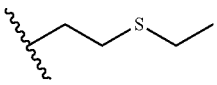 | | |
| 243 | CH₃ | CH₃ | 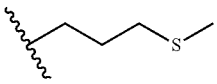 [SMILES: *CCCSC] | | |

TABLE 2-continued
| Number of compound | R₁ | R₂ | R₃ | State | Melting point |
|---|---|---|---|---|---|
| 244 | CH₃ | CH₃ | 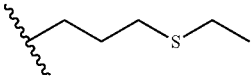 | | |
| 245 | CH₃ | CH₃ | 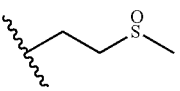 | | |
| 246 | CH₃ | CH₃ | 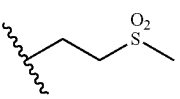 [SMILES: *CCS(C)(=O)=O] | | |
| 247 | CH₃ | CH₃ | 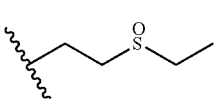 | | |
| 248 | CH₃ | CH₃ | 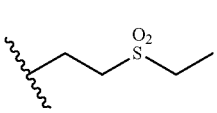 | | |
| 249 | CH₃ | CH₃ |  | Colorless oil | — |
| 250 | CH₃ | CH₃ | 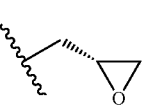 | Colorless oil | — |
| 251 | CH₃ | CH₃ | 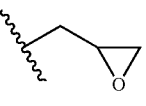 | Colorless oil | — |
| 252 | CH₃ | CH₃ | 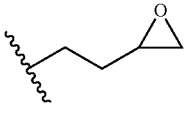 [SMILES: *CCC1CO1] | | |
| 253 | CH₃ | CH₃ | 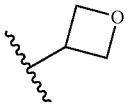 | | |
| 254 | CH₃ | CH₃ | 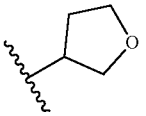 [SMILES: *C1CCOC1] | | |
| 255 | CH₃ | CH₃ | 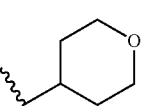 | | |
| 256 | —CH₂CH₂— | | 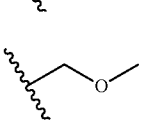 | | |
| 257 | —CH₂CH₂— | | 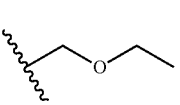 [SMILES: *COCC] | | |

TABLE 2-continued
| Number of compound | R₁ | R₂ | R₃ | State | Melting point |
|---|---|---|---|---|---|
| 258 | | —CH₂CH₂— | 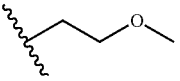 [SMILES: *CCOC] | Colorless oil | — |
| 259 | | —CH₂CH₂— | 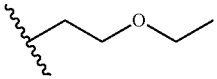 [SMILES: *CCOCC] | | |
| 260 | | —CH₂CH₂— | 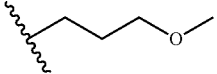 [SMILES: *CCCOC] | | |
| 261 | | —CH₂CH₂— | 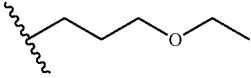 [SMILES: *CCCOCC] | | |
| 262 | | —CH₂CH₂— | 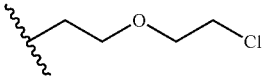 [SMILES: *CCOCCCl] | | |
| 263 | | —CH₂CH₂— | 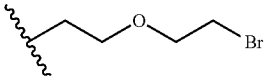 [SMILES: *CCOCCBr] | | |
| 264 | | —CH₂CH₂— | 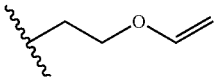 [SMILES: *CCOC=C] | | |
| 265 | | —CH₂CH₂— | 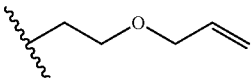 [SMILES: *CCOCC=C] | | |
| 266 | | —CH₂CH₂— | 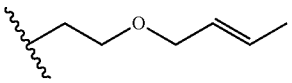 [SMILES: *CCOC/C=C/C] | | |
| 267 | | —CH₂CH₂— | 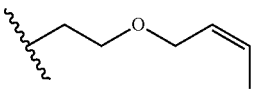 [SMILES: *CCOC/C=C\C] | | |
| 268 | | —CH₂CH₂— | 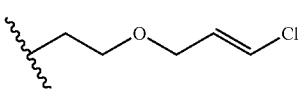 [SMILES: *CCOC/C=C/Cl] | | |
| 269 | | —CH₂CH₂— | 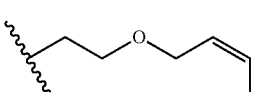 | | |
| 270 | | —CH₂CH₂— | 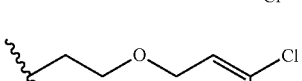 | | |
| 271 | | —CH₂CH₂— | 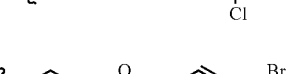 | | |
| 272 | | —CH₂CH₂— | 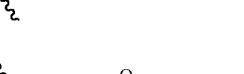 | | |

TABLE 2-continued

| Number of compound | R₁ | R₂ | R₃ | State | Melting point |
|---|---|---|---|---|---|
| 273 | | —CH₂CH₂— | ～～～\_/\_/O\_/ (vinyl ether) | | |
| 274 | | —CH₂CH₂— | ～～～\_/\_/O\_/=/ (allyl ether) | | |
| 275 | | —CH₂CH₂— | ～～～\_/\_/O\_/=\_/ (E-but-2-enyl ether) | | |
| 276 | | —CH₂CH₂— | ～～～\_/\_/O\_/=\ (Z-but-2-enyl ether) | | |
| 277 | | —CH₂CH₂— | ～～～\_/\_/O\_/=\_/Cl (E-3-chloroallyl ether) | | |
| 278 | | —CH₂CH₂— | ～～～\_/\_/O\_/=\Cl (Z-3-chloroallyl ether) | | |
| 279 | | —CH₂CH₂— | ～～～\_/\_/O\_/=CCl₂ (3,3-dichloroallyl ether) | | |
| 280 | | —CH₂CH₂— | ～～～\_/\_/O\_/=\_/Br (E-3-bromoallyl ether) | | |
| 281 | | —CH₂CH₂— | ～～～\_/\_/O\_/=\Br (Z-3-bromoallyl ether) | | |
| 282 | | —CH₂CH₂— | ～～～\_/\_/O\_/≡ (ethynyl ether) | | |
| 283 | | —CH₂CH₂— | ～～～\_/\_/O\_/≡ (propargyl ether) | | |
| 284 | | —CH₂CH₂— | ～～～\_/\_/O\_/≡\_/ (but-2-ynyl ether) | | |
| 285 | | —CH₂CH₂— | ～～～\_/\_/O\_/≡\_/Cl (3-chloropropargyl ether) | | |

TABLE 2-continued
| Number of compound | R₁ | R₂ | R₃ | State | Melting point |
|---|---|---|---|---|---|
| 286 | | —CH₂CH₂— | 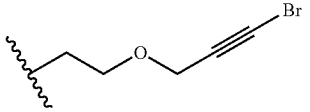 [SMILES: *CCOCC#CBr] | | |
| 287 | | —CH₂CH₂— | 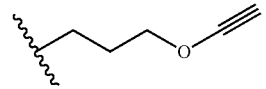 [SMILES: *CCCOC#C] | | |
| 288 | | —CH₂CH₂— | 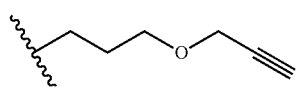 [SMILES: *CCCOCC#C] | | |
| 289 | | —CH₂CH₂— | 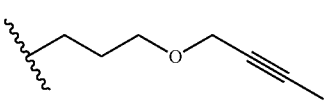 [SMILES: *CCCOCC#CC] | | |
| 290 | | —CH₂CH₂— | 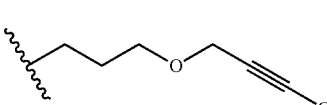 | | |
| 291 | | —CH₂CH₂— | 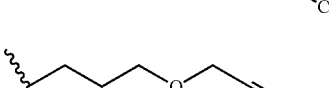 | | |
| 292 | | —CH₂CH₂— | 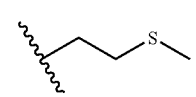 [SMILES: *CCSC] | | |
| 293 | | —CH₂CH₂— | 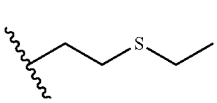 [SMILES: *CCSCC] | | |
| 294 | | —CH₂CH₂— | 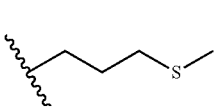 | | |
| 295 | | —CH₂CH₂— | 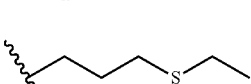 | | |
| 296 | | —CH₂CH₂— | 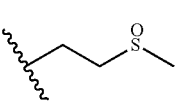 | | |
| 297 | | —CH₂CH₂— | 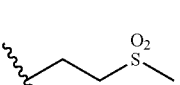 | | |
| 298 | | —CH₂CH₂— | 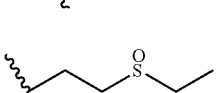 | | |
| 299 | | —CH₂CH₂— | 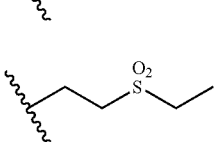 | | |

TABLE 2-continued

| Number of compound | R₁ | R₂ | R₃ | State | Melting point |
|---|---|---|---|---|---|
| 300 | | —CH₂CH₂— | (epoxide) | Colorless oil | — |
| 301 | | —CH₂CH₂— | (epoxide, stereo) | Colorless oil | — |
| 302 | | —CH₂CH₂— | (epoxide) | Colorless oil | — |
| 303 | | —CH₂CH₂— | (epoxide with ethylene linker) | | |
| 304 | | —CH₂CH₂— | (oxetane) | | |
| 305 | | —CH₂CH₂— | (tetrahydrofuran) | | |
| 306 | | —CH₂CH₂— | (tetrahydropyran) | | |

A second aspect of the present invention provides a synthetic method for the foregoing uracil compound containing a carboxylate fragment. Specifically, the method includes a contact reaction between the acid compound shown in formula (II) and a different substituted alcohol, halogenated, or sulfonate compound in the presence of a solvent,

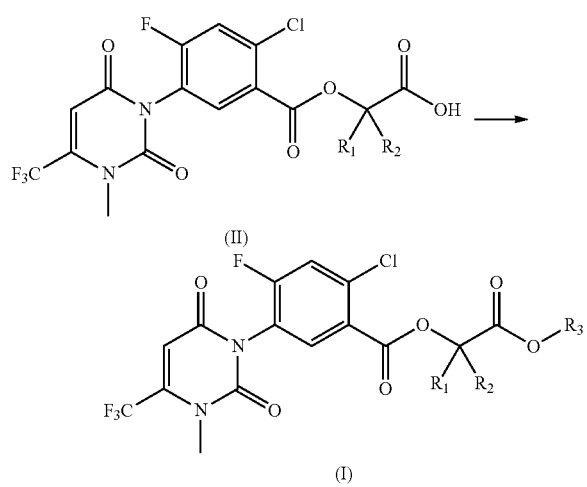

wherein in the general formulas (I) and (II), definitions of $R_1$, $R_2$, and $R_3$ are as follows:

$R_1$ and $R_2$ are selected from hydrogen or methyl respectively; or $R_1$ and $R_2$ together with the carbon atom they are attached form a 3-membered carbocycle.

$R_3$ is selected from $C_{1-3}$ alkoxy $C_{1-3}$ alkyl, $C_{1-3}$ haloalkoxy $C_{1-3}$ alkyl, $C_{2-6}$ alkenoxy $C_{1-3}$ alkyl, $C_{2-6}$ haloalkenoxy $C_{1-3}$ alkyl, $C_{2-6}$ alkynoxy $C_{1-3}$ alkyl, $C_{2-6}$ haloalkynoxy $C_{1-3}$ alkyl, $C_{1-3}$ alkyl S(O)$_n$ $C_{1-3}$ alkyl, $C_{3-6}$ oxygen-containing cycloalkyl $C_{1-3}$ alkyl, or $C_{3-9}$ oxygen-containing cycloalkyl; n=0, 1, or 2.

When $R_1$ is selected from hydrogen and $R_2$ is selected from methyl, the chiral carbon atom connected thereto may be selected from either an R configuration or an S configuration, or a mixture of the two; and in the mixture, a ratio of the R configuration to the S configuration is 1:99 to 99:1.

The reaction temperature is 0-160° C., preferably 20-120° C.; and the time is 2-15 h, preferably 3-12 h.

The reaction solvent is selected from at least one of dichloromethane, 1,2-dichloroethane, tetrahydrofuran, acetonitrile, 1,4-dioxane, toluene, o-xylene, m-xylene, p-xylene, n-heptane, n-octane, and n-nonane.

In the reaction, a molar ratio of the carboxylic acid compound shown in formula (II) to the different substituted alcohol, halogenated, or sulfonate compound is 1:(1-4), preferably 1:(1.1-3).

Some compounds of the general formula (I) of the present invention may be directly obtained through further esterification of the intermediate 1-8.

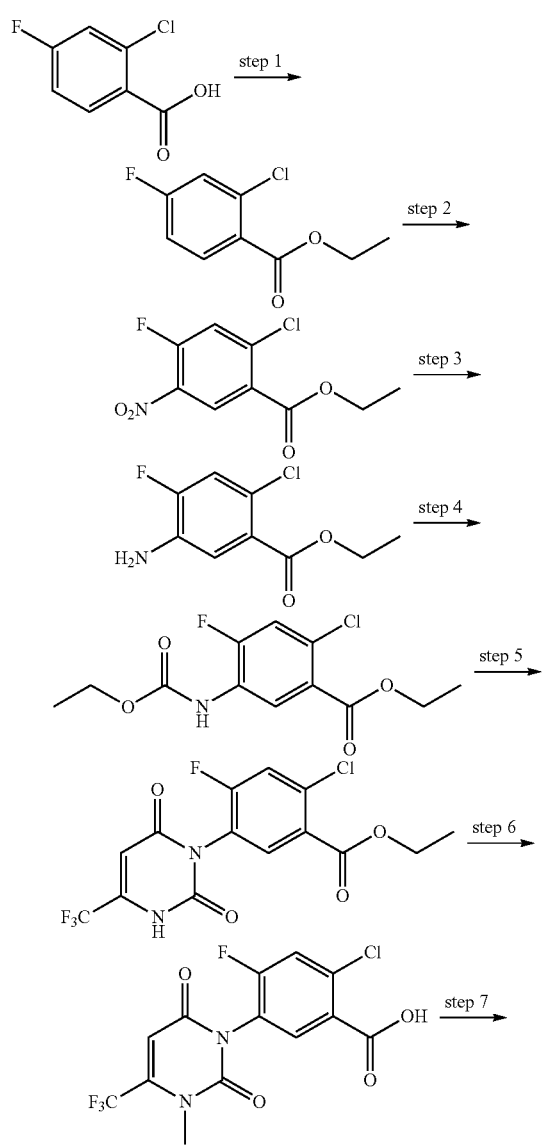
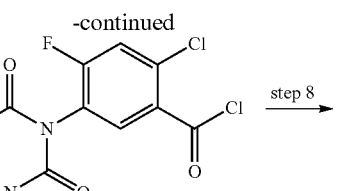
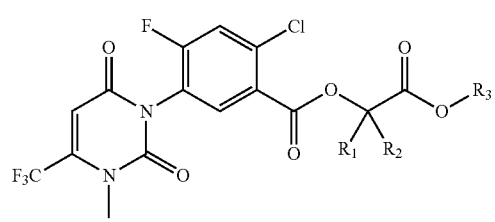

Intermedia 1-8

Some compounds of the general formula (I) of the present invention may also be esterified directly from the intermediate 1-8 to obtain a carboxylic acid of the general formula (II), or a corresponding ester is hydrolyzed to obtain a carboxylic acid of the general formula (II). The carboxylic acid of the general formula (II) may be further prepared into corresponding acyl chlorides, which are then subjected to contact reactions with different substituted alcohols to obtain some compounds of the general formula (I) of the present invention; the carboxylic acid of the general formula (II) may also be subjected to contact reactions with different substituted alcohols through dehydrating agents to obtain some compounds of the general formula (I) of the present invention; and the carboxylic acid of the general formula (II) may also be subjected to contact reactions with halogenated or sulfonate compounds to obtain some compounds of the general formula (I) of the present invention.

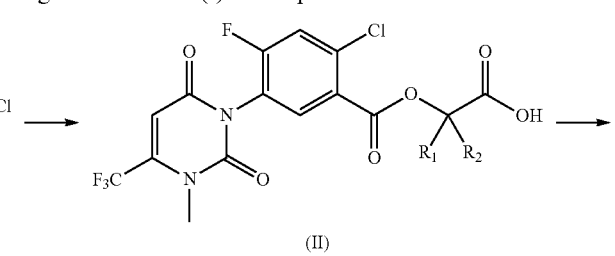
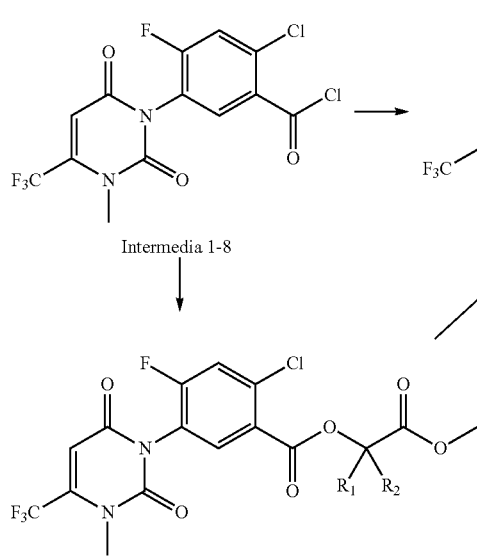

-continued

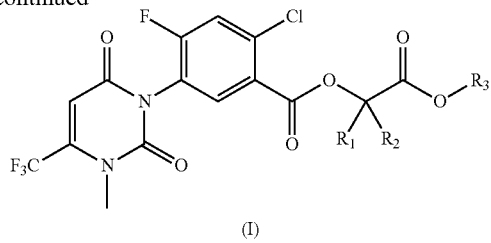

(I)

The reaction is carried out in an appropriate solvent, and the appropriate solvent may be selected from benzene, toluene, xylene, acetone, tetrahydrofuran, acetonitrile, N,N-dimethylformamide, N-methylpyrrolidone, dichloromethane, chloroform, 1,2-dichloroethane, ethyl acetate, or the like. The reaction may be carried out in the presence or absence of an alkali, and when carried out in the presence of an alkali, the reaction may be accelerated. The alkali may be selected from alkali metal hydrides, such as sodium hydride, lithium hydride, or sodium amide; alkali metal hydroxides, such as sodium hydroxide or potassium hydroxide; alkali metal carbonates, such as sodium carbonate or potassium carbonate; and organic alkalies, such as pyridine, 4-dimethylaminopyridine, triethylamine, N-methylpyrrole, or diisopropylethylamine. When a dehydrating agent is used; the dehydrating agent may be 1-ethyl-(3-dimethylaminopropyl) carbodiimide hydrochloride, N,N-dicyclohexylcarbodiimide, or the like. Acyl chlorides may be prepared by using acylation reagents, such as sulfoxide chloride, oxalyl chloride, and the like. The reaction temperature may range from −10° C. to a boiling point temperature of the appropriate solvent used in the reaction, generally 0-100° C. The reaction time is from 30 minutes to 20 hours, generally 1-10 hours.

$R_3$—X or $R_3$—OH is commercially available. X is a leaving group, and is selected from chlorine, bromine, iodine; or sulfonate.

The foregoing method of the present invention may alternatively include necessary pre-treatment operations on the foregoing raw materials and necessary post-treatment operations on reaction products. The operational means of pre-treatment and post-treatment include, but are not limited to, drying, washing, pulping, filtration, centrifugation, column chromatography, recrystallization; and the like. The example section of the present invention provides several specific treatment means, which should not be understood by those skilled in the art as limiting the present invention.

Unless otherwise noted, the definitions of groups in the reaction formula are the same as before.

A third aspect of the present invention provides a use of the uracil compound containing a carboxylate fragment as a herbicide.

A fourth aspect of the present invention provides a herbicidal composition, including a compound of the general formula (I) as an active ingredient, where a weight percentage content of the active ingredient in the composition is 0.1-99.9%.

The compound of the present invention has outstanding herbicidal activity against broad-spectrum economically important monocotyledonous and dicotyledonous annual harmful plants, may effectively control a variety of weeds, may achieve good results at low doses, and may be used as a herbicide. Therefore, the present invention further includes a use of the compounds of the general formula (I) in control of weeds.

Therefore, the present invention relates to a method for preventing and controlling undesired plants or for regulating plant growth, where one or more compounds of the present invention are applied to plants (for example, harmful plants, such as monocotyledonous or dicotyledonous weeds, or undesired crop plants), seeds (for example, grains, seeds, or asexual propagules, such as tubers or young shoots with buds), or plant growth regions (for example, cultivation regions). The compound of the present invention may be applied before planting (by introduction into soil if appropriate), and before or after seedling. The following examples of various representative monocotyledonous and dicotyledonous weed floras prevented and controlled by the compounds of the present invention are only used to illustrate the present invention, but definitely not limit the present invention.

Genera of monocotyledonous harmful plants include *Aegilops, Agropyron, Agrostis, Alopecurus, Apera, Avena, Brachiaria, Bromus, Cenchrus, Commelina, Cynodon, Cyperus, Dactyloctenium, Digitaria, Echinochloa, Eleocharis, Eleusine, Eragrostis, Eriochloa, Festuca, Fimbristylis, Heteranthera, Imperata, Ischaemum, Leptochloa, Lolium, Monochoria, Panicum, Paspalum, Phalaris, Phleum, Poa, Rottboellia, Sagittaria, Scirpus, Setaria*, and *Sorghum*.

Genera of dicotyledonous weeds include *Abutilon, Amaranthus, Ambrosia, Anoda, Anthemis, Aphanes, Artemisia, Atriplex, Bettis, Bidens, Capsella, Carduus, Cassia, Centaurea, Chenopodium, Cirsium, Convolvulus, Datura, Desmodium, Emex, Erysimum, Euphorbia, Galeopsis, Galinsoga, Galium, Hibiscus, Ipomoea, Kochia, Lamium, Lepidium, Lindernia, Matricaria, Mentha, Mercurialis, Mullugo, Myosotis, Papaver, Pharbitis, Plantago, Polygonum, Portulaca, Ranunculus, Raphanus, Rorippa, Rotala, Rumex, Salsola, Senecio, Sesbania, Sida, Sinapis, Solanum, Sonchus, Sphenoclea, Stellaria, Taraxacum, Thlaspi, Trifolium, Urtica, Veronica, Viola*, and *Xanthium*.

When the compound of the present invention is applied to soil before seedling, the growth of harmful plant seeds stops after treatment, and harmful plants stay in a growth period at the time of application, or die completely after a period of time, thereby eliminating competition of weeds harmful to crop plants in a lasting manner at an extremely early time point.

When the compound of the present invention is applied to green plant sites after seedling, the growth stops after treatment, and harmful plants stay in a growth period at the time of application, or die completely after a period of time, thereby eliminating competition of weeds harmful to crop plants in a lasting manner at an extremely early time point.

Therefore, the technical solution of the present invention further includes a use of the compounds of the general formula (I) in control of weeds.

In addition, the compounds of the general formula (I) of the present invention are also applicable to drying and/or defoliation of plants.

As mentioned earlier, the present invention provides a pesticide herbicide, which is composed of an active ingredient and excipients, where the active ingredient includes at least one of the foregoing uracil compounds containing a carboxy late fragment.

Preferably, the content of the active ingredient in the pesticide herbicide is 0.1-99.9 weight %.

The present invention has no special limitations on specific types of the excipients in the herbicide, such as various surfactants and solvents commonly used in the field of herbicides.

For example, the uracil compound containing a carboxylate fragment described in the present invention may be dissolved and diluted with a solvent for later use, and a concentration after dissolution and dilution with the solvent is preferably 0.05-0.4 g/L. The solvent for dissolving the uracil compound containing a carboxylate fragment may include at least one of dimethyl sulfoxide and N,N-dimethylformamide, and a reagent for the dilution may be water containing commonly used additives or the like. Preferably, one or more additives commonly used in herbicides in the art, such as surfactants and emulsifiers, may also be added to the solution in which the uracil compound is dissolved.

In order to enhance the prevention and control effect of the uracil compound containing a carboxylate fragment described in the present invention and increase a use scope thereof, the uracil compound containing a carboxylate fragment of the present invention may be used alone or used with other commonly used herbicides (such as atrazine, tetrazolyl oxalamide, bromoxynil, cyclopentaoxone, and nitrosulfazone). In addition, the proportion of combined use is not specially limited and may be a conventional proportion in the art, as long as the prevention and control effect after the combined use can be enhanced, the use scope can be increased and the safety can be improved.

If there is a conflict between the name of a compound in the present invention and the structural formula, the structural formula shall prevail, except that the structural formula is obviously wrong.

The uracil compound containing a carboxylate fragment provided by the present invention has better herbicidal activity compared with the prior art.

DETAILED DESCRIPTION OF THE EMBODIMENTS

The present invention will be described below in conjunction with examples, but is not limited thereto. In the art, any simple replacement or improvement made by a technician to the present invention falls into the technical solution protected by the present invention.

Example 1: Preparation of Intermediate 1-8

Step 1: Preparation of Intermediate 1-1

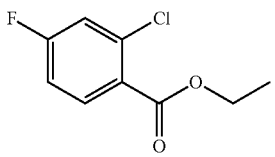

20 g of 2-chloro-4-fluorobenzoic acid and 100 g of ethanol were put into a 500 mL four-necked flask, stirred, and cooled to 0° C., and 17.73 g of sulfoxide chloride was slowly added dropwise, where the temperature was maintained below 0° C. throughout the process. After the sulfoxide chloride was added, the solution was heated to 75° C. and stirred under reflux and reacted overnight, and the reaction solution was spun off to obtain 23.01 g of intermediate 1-1.

Step 2: Preparation of Intermediate 1-2

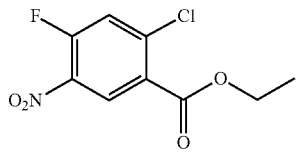 [SMILES: CCOC(=O)c1cc([N+](=O)[O-])c(F)cc1Cl]

67.46 g of intermediate 1-1 and 337.3 g of 1,2-dichloroethane were added to a 1 L four-necked flask and cooled to 0° C., 42.09 g of fuming nitric acid (90%) and 60.12 g of sulfuric acid (98%) were slowly added dropwise, then the solution was slowly heated to room temperature and stirred until the reaction was completed, the reaction solution was transferred to a separating funnel and stood until delamination, an organic phase was taken, an inorganic phase was extracted with 1,2-di chloroethane, the acid in the organic phase was eluted with ice water until the pH value of the aqueous phase was about 7.0, and the solvent was spun off to obtain 89.81 g of crude product. 5 times the mass of n-hexane was added, recrystallization and filtration were carried out, and filter cakes were dried to obtain 42.45 g of intermediate 1-2.

Step 3: Preparation of Intermediate 1-3

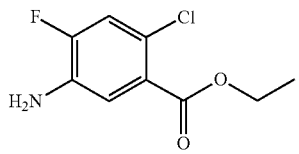

60.84 g of intermediate 1-2, 4.87 g of Pt/C (5%), and 300 mL of ethanol were added into a 1 L autoclave, hydrogen pressure was controlled to 2 MPa, a reaction occurred at 45° C. for 11 hours, then the Pt/C was removed by filtration, and the filtrate was spun off to obtain 52.48 g of crude intermediate 1-3.

Step 4: Preparation of Intermediate 1-4

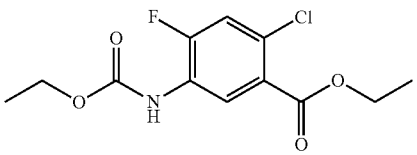 [SMILES: CCOC(=O)Nc1cc(C(=O)OCC)c(Cl)cc1F]

52.48 g of crude intermediate 24.78 g of pyridine, and 262.4 g of dichloromethane were added to a 500 mL four-necked flask and stirred at room temperature, and 34.02 g of ethyl chloroformate was weighed after 5 minutes, diluted with 68.04 g of dichloromethane, and then slowly added dropwise within 1 hour. After reaction for 5 hours, the pH value was adjusted to be weakly acidic, water was added, extraction was carried out with dichloromethane, and the organic phase was spun off to obtain 69.62 g of crude intermediate 1-4.

Step 5: Preparation of Intermediate 1-5

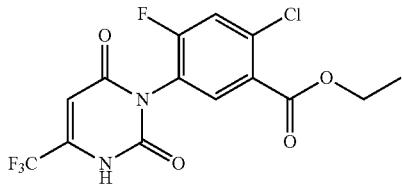 [SMILES: CCOC(=O)c1cc(-n2c(=O)cc(C(F)(F)F)[nH]c2=O)c(F)cc1Cl]

12.98 g of sodium ethanol was dissolved in 38 g of DMF, stirred, and cooled to 5° C. in an ice bath. A DMF (28 g) solution of ethyl 3-amino-4,4,4-trifluorocrotonate (27.95 g) was added dropwise in the ice bath. Then, a DMF solution of 36.84 g of intel mediate 1-4 was added dropwise, and the solution was heated to 100° C. and stirred for 5 h. After the reaction was completed, the pH value was adjusted to be acidic, extraction was carried out with ethyl acetate, the organic phase was washed with saturated salt water and dried with anhydrous sodium sulfate, the solvent was spun off to obtain 50 g of crude product, and the crude product was purified by column chromatography to obtain 19.05 g of intermediate 1-5.

Step 6: Preparation of Intermediate 1-6

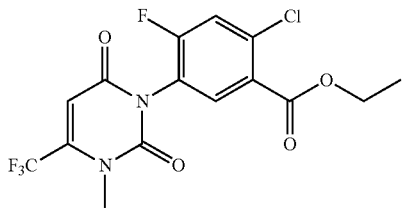 [SMILES: CCOC(=O)c1cc(-n2c(=O)cc(C(F)(F)F)n(C)c2=O)c(F)cc1Cl]

19.05 g of intermediate 1-5 and 8.287 g of anhydrous potassium carbonate were added to a single-necked flask and dissolved with 60 g of THF, and 7.566 g of dimethyl sulfate was added, followed by stirring overnight at room temperature. After the reaction was completed, the THF was spun off, extraction was carried out with ethyl acetate, the anhydrous sodium sulfate was dried, and the organic phase was spun off to obtain 19.62 g of crude intermediate 1-6.

Step 7: Preparation of Intermediate 1-7

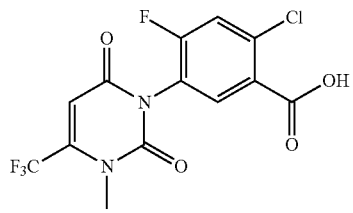 [SMILES: Cn1c(C(F)(F)F)cc(=O)n(-c2cc(C(=O)O)c(Cl)cc2F)c1=O]

19.62 g of intermediate 1-6 was dissolved in 150 mL of glacial acetic acid at room temperature, the same volume of 36% hydrochloric acid was added, and a reflux reaction occurred for 8 h. After the reaction was completed, the excess solvent was evaporated under reduced pressure, and water was added to the residue to precipitate solid, followed by stirring and filtration. Filter cakes were washed with water three times, and dried at 60° C. to obtain 12.73 g of crude intermediate 1-7.

Step 8: Preparation of Intermediate 1-8

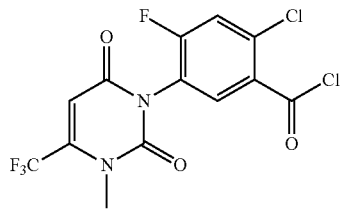 [SMILES: Cn1c(C(F)(F)F)cc(=O)n(-c2cc(C(=O)Cl)c(Cl)cc2F)c1=O]

6.8 g of intermediate 1-7, 35 g of 1,2-dichloroethane, 1 drop of DMF, and 3.316 g of dichlorosulfoxide were added to a 100 ml single-necked flask and subjected to a reflux reaction for 3 h. After the reaction was completed, the excess dichlorosulfoxide and solvent were spun off to obtain 6.22 g of crude intermediate 1-8.

Example 2: Preparation of Compound 3

Step 1: Preparation of Intermediate 3-1

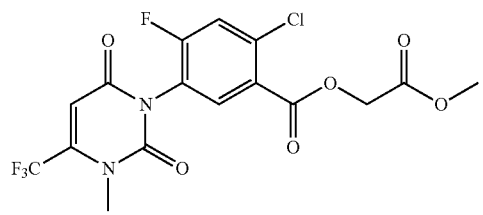 [SMILES: COC(=O)COC(=O)c1cc(-n2c(=O)cc(C(F)(F)F)n(C)c2=O)c(F)cc1Cl]

The intermediate 1-8 (1 g) described in Example 1 and 320 mg of methyl glycolate were added to a reaction flask, cooled in an ice bath, stirred, and blown with nitrogen, 394 mg of triethylamine was added dropwise, and then a reaction occurred at room temperature for 2 h After the reaction was completed, column chromatography purification was carried out to obtain 1.02 g of intermediate 3-1.

Step 2: Preparation of Intermediate 3-2

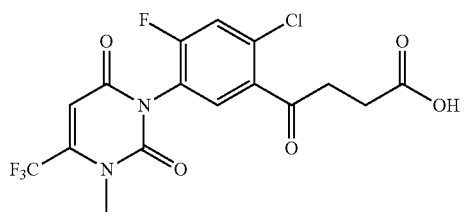 [SMILES: Cn1c(C(F)(F)F)cc(=O)n(-c2cc(C(=O)CCC(=O)O)c(Cl)cc2F)c1=O]

1.02 g of intermediate 3-1, 6.12 g of hydrochloric acid (36%), and 6.12 g of acetic acid were added to a reaction flask and refluxed for 40 min, and the reaction solution was spun off to obtain 1.01 g of intermediate 3-2.

Step 3: Preparation of Intermediate 3-3

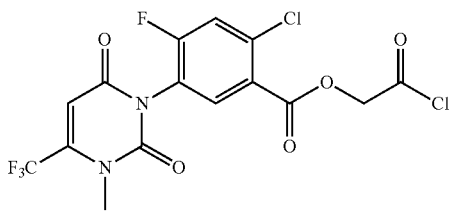 [SMILES: Cn1c(C(F)(F)F)cc(=O)n(-c2cc(C(=O)OCC(=O)Cl)c(Cl)cc2F)c1=O]

1.01 g of intermediate 3-2, 340 mg of dichlorosulfoxide, 2 drops of DMF, and 5.5 g of dichloroethane were added to a reaction flask, a reflux reaction occurred for 3 h, and the reaction solution was spun off to obtain 1.02 g of intermediate 3-3.

Step 4: Preparation of Compound 3

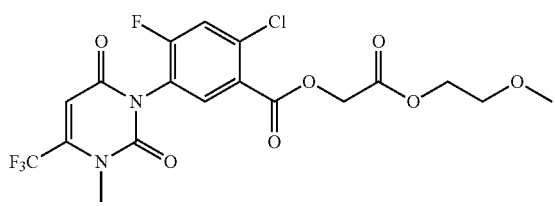

103.29 mg of 2-methoxyethanol and 228.95 mg of triethylamine were added to a reaction flask, cooled in an ice bath, stirred, and blown with nitrogen, 3 mL of dichloromethane solution of the intermediate 3-3 (0.50 g) prepared in the last step was added dropwise, and then a reaction occurred at room temperature for 2 h. After the reaction was completed, column chromatography purification was carried out to obtain 165 mg of compound 3. $^1$H NMR (400 MHz, DMSO-d$_6$) δ 8.16 (d, J=7.8 Hz, 1H), 7.95 (d, J=9.6 Hz, 1H), 6.62 (s, 1H), 4.99 (s, 2H), 4.30-4.23 (m, 2H), 3.59-3.52 (m, 2H), 3.42 (s, 3H), 3.26 (s, 3H). LCMS (ESI) [M+H]$^+$=483.05, Found=482.61.

Example 3: Preparation of Compound 10

Step 1: Preparation of Compound 10

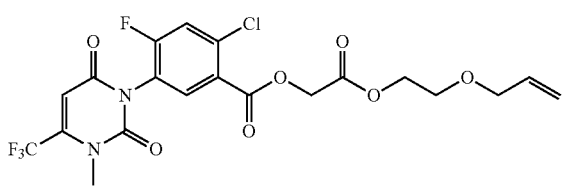

99.83 mg of 2-allyloxyethanol and 123.60 mg of triethylamine were added to a reaction flask, cooled in an ice bath, stirred, and blown with nitrogen, 2.5 mL of dichloromethane solution of the intermediate 3-3 (0.40 g) described in Example 2 was added dropwise, and then a reaction occurred at room temperature for 2 h. After the reaction was completed, column chromatography purification was carried out to obtain 260 mg of light yellow oil as compound NMR (400 MHz, DMSO-d$_6$) δ 8.16 (d, J=7.7 Hz, 1H), 7.94 (d, J=9.6 Hz, 1H), 6.61 (s, 1H), 5.93-5.7 (m, 1H), 5.24 (dq, J=17.4, 1.8 Hz, 1H), 5.13 (dt, J=10.1, 1.6 Hz, 1H), 4.99 (s, 2H), 4.27 (dd, J=5.6, 3.6 Hz, 2H), 3.96 (dt, J=5.4, 1.6 Hz, 2H), 3.67-3.55 (m, 2H). LCMS (ESI) [M+H]$^+$=509.07, Found=508.62.

Example 4: Preparation of Compound 28

Step 1: Preparation of Compound 28

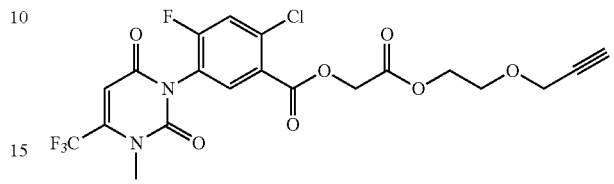

20 mg of propynol ethoxylate and 148.82 mg of triethylamine were added to a reaction flask, cooled in an ice bath, stirred, and blown with nitrogen, 3 nth of dichloromethane solution of the intermediate 3-3 (0.50 g) described in Example 2 was added dropwise, and then a reaction occurred at room temperature for 2 h. After the reaction was completed, column chromatography purification was carried out to obtain 110 mg of light yellow oil as compound 28. $^1$H NMR (400 MHz, DMSO-d$_6$) δ 8.15 (d, J=7.7 Hz, 1H), 7.94 (d, J=9.6 Hz, 1H), 6.61 (s, 1H), 4.98 (s, 2H), 4.27 (dd, J=5.7, 3.4 Hz, 2H), 4.16 (d, J=2.4 Hz, 2H), 3.75-3.63 (m, 2H), 3.43 (d, J=11.5 Hz, 4H). LCMS (ESI) [M+H]$^+$=507.05, Found=506.83.

Example 5: Preparation of Intermediate 54-3

Step 1: Preparation of Intermediate 54-1

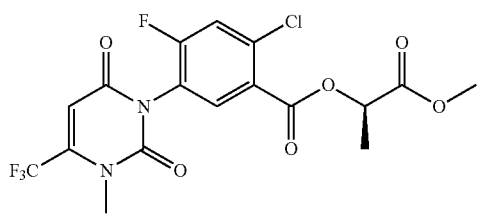 [SMILES: COC(=O)[C@@H](C)OC(=O)c1cc(-n2c(=O)cc(C(F)(F)F)n(C)c2=O)c(F)cc1Cl]

20 g of the intermediate 1-8 described in Example 1, 4.86 g of methyl D-lactate, and 100 g of dichloromethane were added to a reaction flask, blown with nitrogen, and stirred at room temperature. 5.9 g of triethylamine was added dropwise within 60 min, followed by stirring overnight at room temperature. After the reaction was completed, column chromatography purification was carried out to obtain 16 g of intermediate 54-1.

Step 2: Preparation of Intermediate 54-2

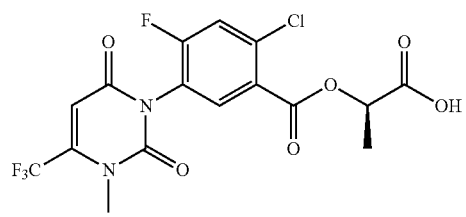 [SMILES: C[C@@H](OC(=O)c1cc(-n2c(=O)cc(C(F)(F)F)n(C)c2=O)c(F)cc1Cl)C(=O)O]

15 g of intermediate 54-1, 90 g of hydrochloric acid (36%), and 90 g of acetic acid were added into a reaction flask and stirred at 60° C. for 40 min until the reaction ended, and the solvent was spun off to obtain 14 g of intermediate 54-2.

Step 3: Preparation of Intermediate 54-3

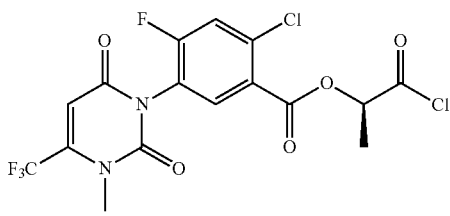 [SMILES: C[C@@H](OC(=O)c1cc(-n2c(=O)cc(C(F)(F)F)n(C)c2=O)c(F)cc1Cl)C(=O)Cl]

5.0 g of intermediate 54-2, 1.63 g of sulfoxide chloride, 25 g of 1,2-dichloroethane, and 2 drops of DMF were added into a reaction flask for reflux stirring at 90° C. After one hour of reaction, the solvent was spun off to obtain 5.1 g of intermediate 54-3.

Example 6: Preparation of Compound 54

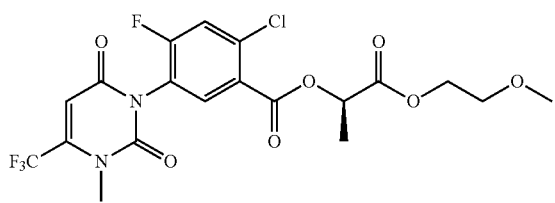

0.6 g of the intermediate 54-3 described in Example 5, 0.120 g of 2-n ethoxyethanol, 10 g of dichloromethane, and 0.2 g of triethylamine were added to a reaction flask, blown with nitrogen, and stirred at room temperature for 1 h until the reaction ended. After the reaction was completed, column chromatography purification was carried out to obtain 0,350 g of compound 54. $^1$H NMR (400 MHz, CDCl$_3$) δ 7.97 (dd, J=7.7, 2.0 Hz, 1H), 7.40 (d, J=9.2 Hz, 1H), 6.37 (s, 1H), 5.36 (q, J=7.0 Hz, 1H), 4.32 (s, 2H), 3.60 (t, J=4.6 Hz, 2H), 3.57 (s, 3H), 3.36 (s, 3H), 1.62 (d, J=7.1 Hz, 3H). LCMS (ESI) [M+H]$^+$=497.07, Found=497.16.

Example 7: Preparation of Compound 61

Step 1: Preparation of Compound 61

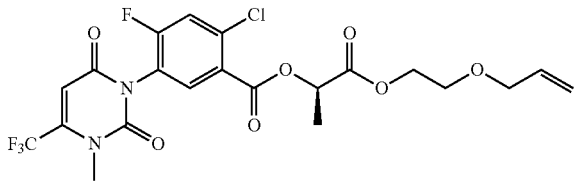 [SMILES: C=CCOCCOC(=O)[C@@H](C)OC(=O)c1cc(-n2c(=O)cc(C(F)(F)F)n(C)c2=O)c(F)cc1Cl]

290 mg of 2-allyloxyethanol and 330 mg of triethylamine were added to a reaction flask, cooled in an ice bath, stirred, and blown with nitrogen, 10 ML of dichloromethane solution of the intermediate 54-3 (1.0 g) described in Example 5 was added dropwise, and then a reaction occurred at room temperature for 1 h. After the reaction was completed, column chromatography purification was carried out to obtain 800 mg of compound 61. $^1$H NMR (400 MHz, DMSO-d$_6$) δ 8.14 (d, J=7.8 Hz, 1H), 7.94 (d, J=9.6 Hz, 1H), 6.62 (d, J=3.0 Hz, 1H) (ddtd, J=16.9, 10.6, 5.3, 1.1 Hz, 1H), 5.31 (qt, J=6.5, 3.3 Hz, 1H), 5.26-5.20 (m, 1H), 5.12 (dq, J=10.4, 1.6 Hz, 1H), 4.34-4.20 (m, 2H), 3.95 (dt, J=5.3, L5 Hz, 2H), 3.60 (ddd, J=6.0, 4.2, 1.4 Hz, 2H), 3.45-3.40 (m, 3H), 1.53 (d, J=7.0 Hz, 3H). LCMS (ESI) [M+H]$^+$=523.08, Found=522.96.

Example 8: Preparation of Compound 79

Step 1: Preparation of Compound 79

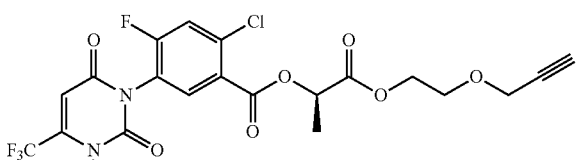

1 g of the intermediate 54-3 described in Example 5 was dissolved in 5 mL of 1,2-dichloroethane, a 1,2-dichloroethane solution of propynol ethoxylate (220 mg) was added dropwise, the solution was stirred at 20° C. for 10 minutes, and then 330 mg of triethylamine was added dropwise. After the reaction of the raw materials was completed upon LCMS test, mL of hydrochloric acid (1N) was added for washing, the solution was separated, the organic phase was dried with anhydrous sodium sulfate, and column chromatography purification was carried out to obtain 200 mg of colorless oily liquid as compound 79. $^1$H NMR (400 MHz, Chloroform-d) δ 7.97 (dd, J=7.7, 2.1 Hz, 1H), 7.40 (d, J=9.2 Hz, 1H), 6.38 (d, =LO Hz, 1H), 5.36 (q, J=7.1 Hz, 1H), 5.30 (s, 1H), 4.17 (dd, J=2.4, 0.7 Hz, 2H), 3.76 (dt, J=6.9, 3.0 Hz, 2H), 3.59-3.55 (m, 3H), 1.62 (dd, J=7.1, 1.0 Hz, 3H), 1.33-1.23 (m, 2H). LCMS (ESI) [M+H]$^+$=521.07, Found=521.21.

Example 9: Preparation of Compound 88

Step 1: Preparation of Compound 88

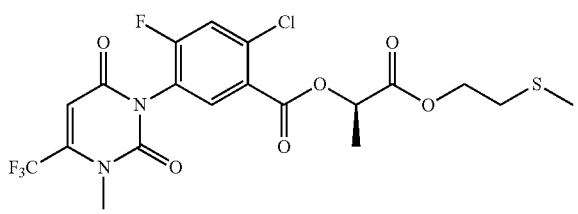 [SMILES: CSCCOC(=O)[C@@H](C)OC(=O)c1cc(-n2c(=O)cc(C(F)(F)F)n(C)c2=O)c(F)cc1Cl]

145.14 mg of 2-(methylthio)ethanol and 199.21 mg of triethylamine were added to a reaction flask, cooled in an ice bath, stirred, and blown with nitrogen, 3 mL of dichloromethane solution of the intermediate 54-3 (0.60 g) described in Example 5 was added dropwise, and then a reaction occurred at room temperature for 2 h. After the reaction was completed, column chromatography purification was carried out to obtain 545 mg of colorless oil as compound 88. $^1$H NMR (400 MHz, DMSO-d$_6$) δ 8.15 (d, J=7.8 Hz, 1H), 7.94 (d, J=9.6 Hz, 1H), 6.63 (d, =2.9 Hz, 1H), 5.32 (dd, J=7.0, 2.0 Hz, 1H), 4.39-4.21 (m, 2H), 3.42 (s, 3H), 2.83-2.66 (m, 2H), 2.11-2.07 (m, 3H), 1.55 (d, J=7.0 Hz, 3H). LCMS (ESI) [M+H]$^+$=512.04, Found=512.54.

Example 10: Preparation of Compound 92

Step 1: Preparation of Compound 92

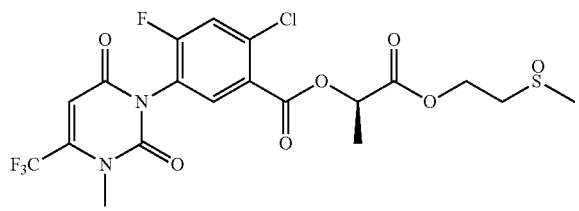

250.0 mg of compound 88 and 10 mL of dichloromethane were added to a reaction flask, cooled in an ice bath, stirred, and blown with nitrogen, 84.11 mg of m-chloroperoxybenzoic acid was added, and then a reaction occurred at room temperature for 2 h. After the reaction was completed, column chromatography purification was carried out to obtain 177 mg of colorless oil as compound 92. $^1$H NMR (400 MHz, DMSO-$d_6$) δ 8.22 (d, J=7.7 Hz, 1H), 8.01 (d, J=9.6 Hz, 1H), 6.70 (d, J=2.9 Hz, 1H), 5.45-5.35 (m, 1H), 4.66-4.42 (m, 2H), 3.49 (s, 3H), 3.29-3.02 (m, 2H), 2.73-2.62 (m, 3H), 1.61 (d, J=7.0 Hz, 3H). LCMS (ESI) [M+H]$^+$=529.04, Found=528.65.

Example 11: Preparation of Compound 93

Step 1: Preparation of Compound 93

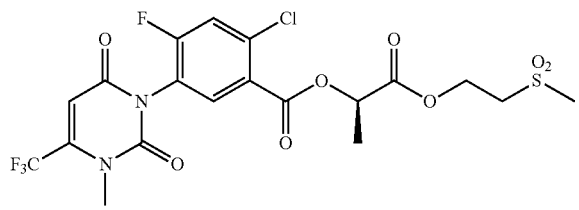

97.77 mg of 2-methylsulfonyl ethanol and 99.61 mg of triethylamine were added to a reaction flask, cooled in an ice bath, stirred, and blown with nitrogen, 2 mL of dichloromethane solution of the intermediate 54-3 (0.30 g) described in Example 5 was added dropwise, and then a reaction occurred at room temperature for 2 h. After the reaction was completed, column chromatography purification was carried out to obtain 192 mg of compound 93. $^1$H NMR (400 MHz, DMSO-$d_6$) δ 8.16 (d, J=7.7 Hz, 1H), 7.94 (d, J=9.5 Hz, 1H), 6.63 (d, J=3.2 Hz, 1H), 5.44-5.28 (m, 1H), 4.57-4.41 (m, 2H), 3.55 (t, J=5.8 Hz, 2H), 3.02 (s, 3H), 1.54 (d, J=7.0 Hz, 3H). LCMS (EST) [M+H]$^+$=545.03, Found=544.58.

Example 12: Preparation of Compound 96

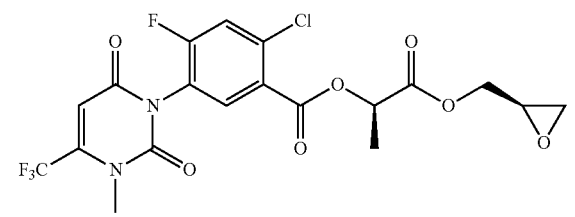

0.5 g of the intermediate 53-3 described in Example 5, 5 mL of dichloromethane, 97.2 mg of (S)-glycidol, and 0.17 g of triethylamine were added to a 25 mL single-necked flask, and stirred overnight at room temperature. After the reaction was completed, 5 mL of water was added, the solution was stirred and separated to obtain an organic phase, the organic phase was dried with anhydrous sodium sulfate, and the solvent was evaporated under reduced pressure. Column chromatography purification was carried out to obtain 215 mg of compound 96. $^1$H NMR (400 MHz, CDCl$_3$) δ 7.97 (d, J=7.7 Hz, 1H), 7.40 (d, 0.1=9.1 Hz, 1H), 6.38 (d, J=1.1 Hz, 1H), 5.37 (q, J=7.0 Hz, 1H), 4.49 (dd, J=12.2, 3.0 Hz, 1H), 4.07-3.94 (m, 1H), 3.57 (s, 3H), 3.22 (tt, J=9.8, 4.9 Hz, 1H), 2.84 (q, J=4.4 Hz, 1H), 2.63 (dd, J=4.7, 2.6 Hz, 1H), 1.62 (t, J=9.2 Hz, 3H). LCMS (ESI) [M+H]$^+$=495.05, Found=495.05.

Example 13: Preparation of Compound 97

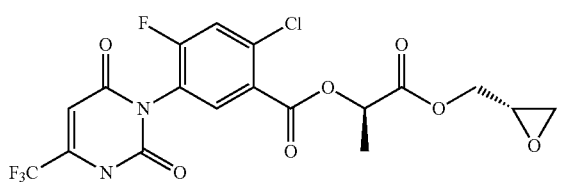

0.5 g of the intermediate 53-3 described in Example 5, 5 mL of dichloromethane, 97.2 mg of (R)-glycidol, and 0.17 g of triethylamine were added to a 25 mL single-necked flask, and stirred overnight at room temperature. After the reaction was completed, 5 mL of water was added, the solution was stirred and separated to obtain an organic phase, the organic phase was dried with anhydrous sodium sulfate, and the solvent was evaporated under reduced pressure. Column chromatography purification was carried out to obtain 330 mg of compound 97. $^1$H NMR (400 MHz, CDCl$_3$) δ 7.97 (d, J=7.7 Hz, 1H), 7.40 (d, J=9.2 Hz, 1H), 6.37 (d, J=2.3 Hz, 1H), 5.37 (qd, J=7.1, 2.2 Hz, 1H), 4.49 (dd, J=12.2, 2.2 Hz, 1H), 4.13-3.98 (m, 1H), 3.57 (d, J=2.0 Hz, 3H), 3.20 (tt, J=5.7, 2.8 Hz, 1H), 2.84 (t, J=4.5 Hz, 1H), 2.67 (dt, J=5.6 Hz, 1H), 1.63 (d, J=7.1 Hz, 3H). LCMS (ESI) [M+H]$^+$=495.05, Found=495.30.

Example 14: Preparation of Intermediate 105-3

Step 1: Preparation of Intermediate 105-1

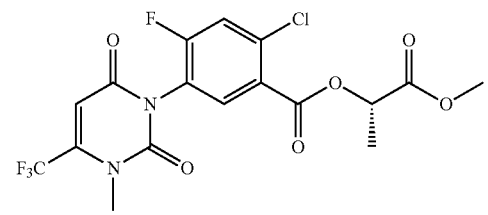 [SMILES: COC(=O)[C@H](C)OC(=O)c1cc(-n2c(=O)cc(C(F)(F)F)n(C)c2=O)c(F)cc1Cl]

324.4 mg of methyl L-lactate was added to a reaction flask, cooled in an ice bath, stirred, and blown with nitrogen, and the intermediate 1-8 (1 g) described in Example 1 was added dropwise, followed by 394 mg of triethylamine. Then, a reaction occurred at room temperature for 2 h. After the reaction was completed, column chromatography purification was carried out to obtain 923 mg of intermediate 105-1.

Step 2: Preparation of Intermediate 105-2

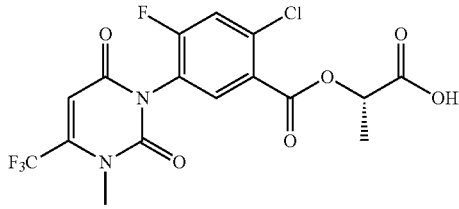 [SMILES: C[C@H](OC(=O)c1cc(-n2c(=O)cc(C(F)(F)F)n(C)c2=O)c(F)cc1Cl)C(=O)O]

923 mg of intermediate 105-1, 6.46 g of hydrochloric acid (36%), and 6.46 g of acetic acid were added to a reaction flask and refluxed for 40 min, and the reaction solution was spun off to obtain 900 mg of intermediate 105-2.

Step 3: Preparation of Intermediate 105-3

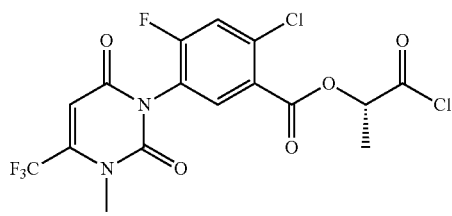 [SMILES: C[C@H](OC(=O)c1cc(-n2c(=O)cc(C(F)(F)F)n(C)c2=O)c(F)cc1Cl)C(=O)Cl]

900 mg of intermediate 105-2, 366.49 mg of dichlorosulfoxide, 2 drops of DMF, and 4.5 g of 1,2-dichloroethane were added to a reaction flask, a reflux reaction occurred for 3 h, and the reaction solution was spun off to obtain 800 mg of intermediate 105-3.

Example 15: Preparation of Compound 105

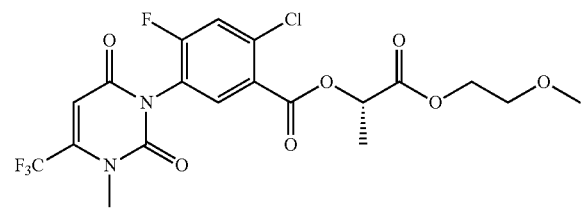 [SMILES: COCCOC(=O)[C@H](C)OC(=O)c1cc(-n2c(=O)cc(C(F)(F)F)n(C)c2=O)c(F)cc1Cl]

0.6 g of the intermediate 105-3 described in Example 14, 0.120 g of 2-methoxyethanol, g of dichloromethane, and 0.2 g of triethylamine were added to a reaction flask, blown with nitrogen, and stirred at room temperature for 1 h until the reaction ended. After the reaction was completed, column chromatography purification was carried out to obtain 0.40 g of compound 105. $^1$H NMR (400 MHz, CDCl$_3$) δ 7.97 (dd, J=7.7, 2.0 Hz, 1H), 7.40 (d, J=9.2 Hz, 1H), 6.37 (s, 1H), 5.36 (q, J=7.0 Hz, 1H), 4.32 (s, 2H), 3.60 (t, J=4.6 Hz, 2H), 3.57 (s, 3H), 3.36 (s, 3H), 1.62 (d, J=7.0 Hz, 3H). LCMS (ESI) [M+H]$^+$=497.07 Found=497.34.

Example 16: Preparation of Compound 112

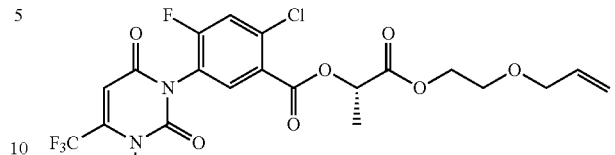

The intermediate 105-3 (1 g) described in Example 14 was weighed into a 25 ml single-necked flask, and 10 mL of dichloromethane, 268 mg of 2-allyloxyethanol, and 330 mg of triethylamine were added, followed by stirring at room temperature for reaction. After 15 h, the reaction ended upon LCMS test. 5 mL of water was added, and the solution was stirred and separated to obtain an organic phase. The organic phase was dried, and the excess solvent was evaporated under reduced pressure. After column chromatography purification (PE:EA=4:1), 768 mg of colorless oily liquid was obtained as compound 112. $^1$H NMR (400 MHz, CDCl$_3$) δ 7.97 (dd, J=7.7, 1.9 Hz, 1H), 7.40 (d, J=9.2 Hz, 1H), 6.37 (s, 1H), 5.87 (ddd, J=22.7, 10.7, Hz, 1H), 5.35 (t, J=7.0 Hz, 1H), 5.27 (dd, J=17, 2, 1.5 Hz, 1H), 5.18 (d, J=10.4 Hz, 1H), 4.43-4.24 (m, 2H), 4.00 (d, J=5.4 Hz, 2H), 3.65 (t, J=4.8 Hz, 2H), 3.57 (s, 3H), 1.62 (d, J=7.1 Hz, 3H). LCMS (ESI) [M+H]$^+$=523.08, Found=523.10.

Example 17: Preparation of Compound 130

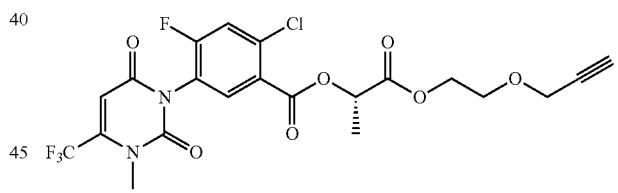

1 g of the intermediate 105-3 described in Example 14 was dissolved in 5 mL of 1,2-dichloroethane, a 1,2-dichloroethane solution of propynol ethoxylate (220 mg) was added dropwise, the solution was stirred at 20° C. for 10 minutes, and then 330 mg of triethylamine was added dropwise. After the reaction of the raw materials was completed upon LCMS test, mL of hydrochloric acid (1N) was added for washing, the solution was separated, the organic phase was dried with anhydrous sodium sulfate, and column chromatography purification was carried out to obtain 230 mg of colorless oily liquid as compound 130. $^1$H NMR (400 MHz, Chloroform-d) δ 7.97 (dd, J=7.7, 2.1 Hz, 11-1), 7.40 (d, J=9.2 Hz, 1H), 6.38 (d, J=1.0 Hz, 1H), 5.36 (q, J=7.1 Hz, 1H), 5.30 (s, 1H), 4.17 (dd, J=2.4, 0.7 Hz, 2H, 3.76 (dt, J=6.9, 3.0 Hz, 2H), 3.59-3.55 (m, 3H), 1.62 (dd, J=7.1, 1.0 Hz, 3H), 1.33-1.23 (m, 2H). LCMS (ESI) [M+H]$^+$=521.07, Found=521.12.

Example 18: Preparation of Compound 139

Step 1: Preparation of Compound 139

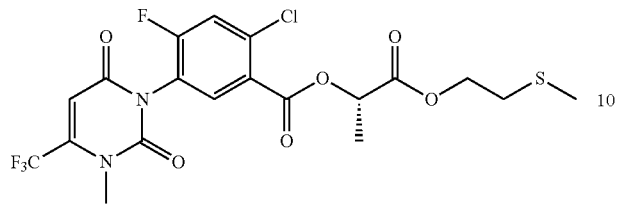

145.14 mg of 2-(methylthio)ethanol and 199.21 mg of triethylamine were added to a reaction flask, cooled in an ice bath, stirred, and blown with nitrogen, 3 mL of dichloromethane solution of the intermediate 105-3 (0.60 g) described in Example 14 was added dropwise, and then a reaction occurred at room temperature for 2 h. After the reaction was completed, column chromatography purification was carried out to obtain 419 mg of colorless oil as compound 139. $^1$H NMR (400 MHz, DMSO-d$_6$) δ 8.15 (d, J=7.8 Hz, 1H), 7.94 (d, J=9.6 Hz, 1H), 6.63 (d, J=2.9 Hz, 1H), 5.32 (dd, J=7.0, 2.0 Hz, 1H), 4.39-4.21 (m, 2H), 3.42 (s, 3H), 2.83-2.66 (m, 2H), 2.11-2.07 (m, 3H), 1.55 (d, J=7.0 Hz, 3H). LCMS (ESI) [M+H]$^+$=512.04, Found=512.54.

Example 19: Preparation of Compound 143

Step 1: Preparation of Compound 143

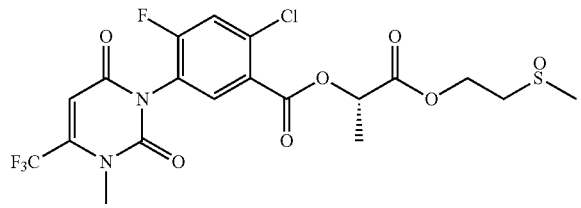

250.0 mg of the compound 139 described in Example 18 and 10 mL of dichloromethane were added to a reaction flask, cooled in an ice bath, stirred, and blown with nitrogen, 84.11 mg of m-chloroperoxybenzoic acid was added, and then a reaction occurred at room temperature for 2 h. After the reaction was completed, column chromatography purification was carried out to obtain 170 mg of colorless oil as compound 143. $^1$H NMR (400 MHz, DMSO-d$_6$) δ 8.21 (d, J=7.7 Hz, 1H), 8.01 (d, J=9.6 Hz, 1H), 6.70 (d, J=2.8 Hz, 1H), 5.41 (qt, J=7.2, 1.6 Hz, 1H), 4.70-4.43 (m, 2H), 3.48 (s, 3H), 3.27-3.00 (m, 2H), 2.65 (d, J=2.6 Hz, 3H), 1.61 (d, J=7.0 Hz, 3H). LCMS (ESI) [M+H]$^+$=529.04, Found=528.65.

Example 20: Preparation of Compound 144

Step 1: Preparation of Compound 144

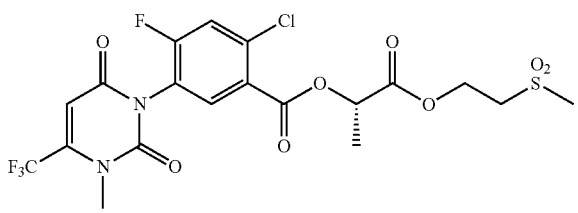 [SMILES: C[C@H](OC(=O)c1cc(-n2c(=O)cc(C(F)(F)F)n(C)c2=O)c(F)cc1Cl)C(=O)OCCS(C)(=O)=O]

97.77 mg of 2-methylsulfonyl ethanol and 99.61 mg of triethylamine were added to a reaction flask, cooled in an ice bath, stirred, and blown with nitrogen, 2 mL, of dichloromethane solution of the intermediate 105-3 (0.30 g) described in Example 14 was added dropwise, and then a reaction occurred at room temperature for 2 h. After the reaction was completed, column chromatography purification was carried out to obtain 166 mg of compound 144. $^1$H NMR (400 MHz, DMSO-d$_6$) δ 8.16 (d, J=7.7 Hz, 1H), 7.94 (d, J=9.5 Hz, 1H), 6.63 (d, J=3.2 Hz, 1H), 5.43-5.32 (m, 1H), 4.57-4.41 (m, 2H), 3.55 (t, J=5.8 Hz, 2H), 3.02 (s, 3H), 1.54 (d, J=7.2 Hz, 3H). LCMS (ESI) [M+H]$^+$=545.03, Found=544.58.

Example 21: Preparation of Compound 147

0.5 g of the intermediate 105-3 described in Example 14, 5 mL of dichloromethane, 97.2 mg of (S)-glycidol, and 0.17 g of triethylamine were added to a 25 mL single-necked flask, and stirred overnight at room temperature. After the reaction was completed, 5 mL of water was added, the solution was stirred and separated to obtain an organic phase, the organic phase was dried with anhydrous sodium sulfate, and the solvent was evaporated under reduced pressure. Column chromatography purification was carried out to obtain 215 mg of compound 147. $^1$H NMR (400 MHz, CDCl$_3$) δ 7.97 (d, J=7.7 Hz, 1H), 7.40 (d, J=9.1 Hz, 1H), 6.38 (d, J=1.1 Hz, 1H), 5.37 (q, J=7.0 Hz, 1H), 4.49 (dd, J=12.2, 3.0 Hz, 1H), 4.07-3.94 (m, 1H), 3.57 (s, 3H), 3.22 (tt, J=9.8, 4.9 Hz, 1H), 2.84 (q, J=4.4 Hz, 1H), 2.63 (dd, J=4.7, 2.6 Hz, 1H), 1.62 (t, J=9.2 Hz, 3H). LCMS (ESI) [M+H]$^+$=495.05, Found=495.12.

Example 22: Preparation of Compound 148

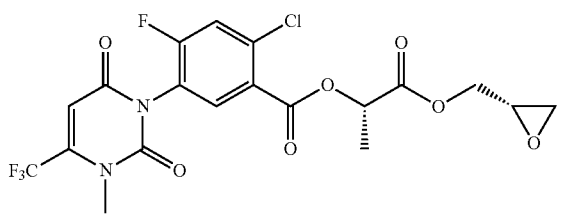 [SMILES: C[C@H](OC(=O)c1cc(-n2c(=O)cc(C(F)(F)F)n(C)c2=O)c(F)cc1Cl)C(=O)OC[C@@H]1CO1]

0.5 g of the intermediate 105-3 described in Example 14, 5 mL of dichloromethane, 97.2 mg of (R)-glycidol, and 0.17 g of triethylamine were added to a 25 mL single-necked flask, and stirred overnight at room temperature. After the reaction was completed, 5 mL of water was added, the solution was stirred and separated to obtain an organic phase, the organic phase was dried with anhydrous sodium sulfate, and the solvent was evaporated under reduced pressure. Column chromatography purification was carried out to obtain 240 mg of compound 148. $^1$H NMR (400 MHz, CDCl$_3$) δ 7.97 (d, J=7.7 Hz, 1H), 7.40 (d, J=9.1 Hz, 1H), 6.37 (d, J=2.2 Hz, 1H), 5.37 (dd, J=7.1, 2.1 Hz, 1H), 4.49 (dd, J=12.2, 2.3 Hz, 1H), 4.07 (ddd, J=12.2, 5.9, 2.0 Hz, 1H), 3.57 (d, J=1.9 Hz, 3H), 3.20 (tt, J=5.8, 2.8 Hz, 1H), 2.83 (t, J=4.5 Hz, 1H), 2.72-2.62 (m, 1H), 1.63 (d, J=7.1 Hz, 3H). LCMS (ESI) [M+H]$^+$=495.05, Found=495.06.

Example 23: Preparation of Intermediate 156-3

Step 1: Preparation of Intermediate 156-1

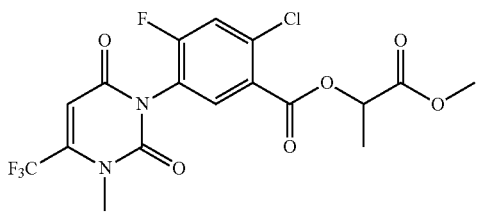 [SMILES: COC(=O)C(C)OC(=O)c1cc(-n2c(=O)cc(C(F)(F)F)n(C)c2=O)c(F)cc1Cl]

20.0 g of the intermediate 1-8 described in Example 1, 4.86 g of methyl lactate, and 100 g of dichloromethane were added to a reaction flask, blown with nitrogen, and stirred at room temperature. 5.9 g of triethylamine was added dropwise within 60 min, followed by stirring overnight at room temperature. After the reaction was completed, column chromatography purification was carried out to obtain 15.8 g of intermediate 156-1.

Step 2: Preparation of Intermediate 156-2

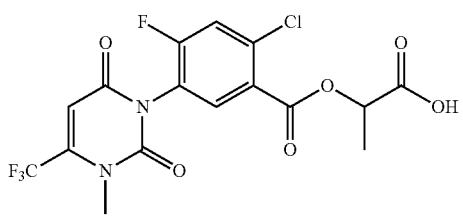

15.0 g of intermediate 22-1, 90 g of hydrochloric acid (36%), and 90 g of acetic acid were added into a reaction flask and stirred at 60° C. for 40 min until the reaction ended, and the solvent was spun off to obtain 13.7 g of intermediate 156-2.

Step 3: Preparation of Intermediate 156-3

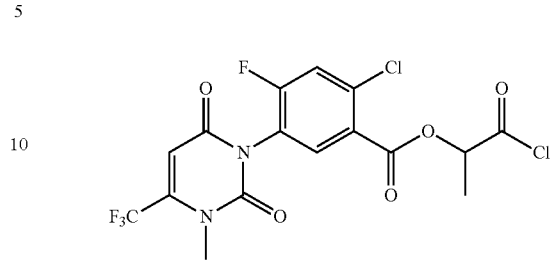

900 mg of intermediate 156-2, 366.49 mg of dichlorosulfoxide, 2 drops of DMF, and 4.5 of 1,2-dichloroethane were added to a reaction flask, a reflux reaction occurred for 3 h, and the reaction solution was spun off to obtain 820 mg of intermediate 156-3.

Example 24: Preparation of Compound 156

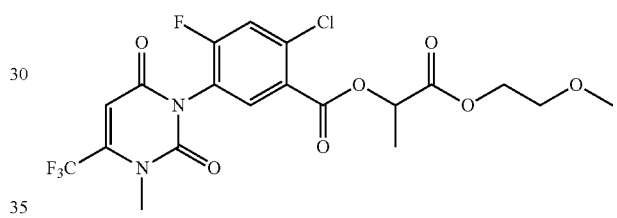

0.6 g of the intermediate 156-3 described in Example 23, 0.120 g of 2-methoxyethanol, g of dichloromethane, and 0.2 g of triethylamine were added to a reaction flask, blown with nitrogen, and stirred at room temperature for 1 h until the reaction ended. After the reaction was completed, column chromatography purification was carried out to obtain 0.395 g of compound 156. $^1$H NMR (400 MHz, CDCl$_3$) δ 7.97 (dd, J=7.7, 2.0 Hz, 1H), 7.40 (d, J=9.2 Hz, 1H), 6.37 (s, 1H), 5.36 (q, J=7.0 Hz, 1H), 4.32 (s, 2H), 3.60 (t, J=4.6 Hz, 2H), 3.57 (s, 3H), 3.36 (s, 3H), 1.62 (d, J=7.0 Hz, 3H). LCMS (ESI) [M+H]$^+$=497.07, Found=497.30.

Example 25: Preparation of Compound 163

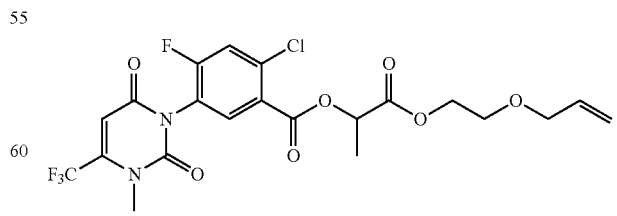

With reference to the methods of Examples 7 and 16, compound 163 was prepared by using the intermediate 156-3 described in Example 23 and 2-allyloxyethanol.

Example 26: Preparation of Compound 181

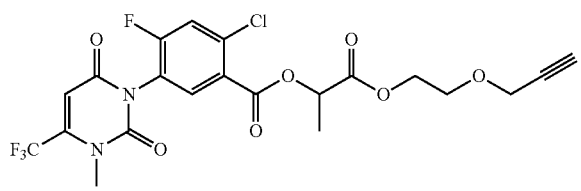 [SMILES: C#CCOCCOC(=O)C(C)OC(=O)c1cc(-n2c(=O)cc(C(F)(F)F)n(C)c2=O)c(F)cc1Cl]

With reference to the methods of Examples 8 and 17, compound 181 was prepared by using the intermediate 156-3 described in Example 23 and propynol ethoxylate. $^1$H NMR (400 MHz, Chloroform-d) δ 7.97 (dd, J=7.7, 2.1 Hz, 1H), 7.40 (d, J=9.2 Hz, 1H), 6.38 (d, J=1.0 Hz, 1H), 5.36 (q, J=7.1 Hz, 1H), 5.30 (5, 1H), 4.17 (dd, J=2.4, 0.7 Hz, 2H), 3.76 (dt, J=6.9, 3.0 Hz, 2H), 3.59-3.55 (m, 3H), 1.62 (dd, J=7.1, 1.0 Hz, 3H), 1.33-1.23 (m, 2H), LCMS (ESI) [M+H]$^+$=521.07, Found=521.11.

Example 27: Preparation of Compound 190

Step 1: Preparation of Compound 190

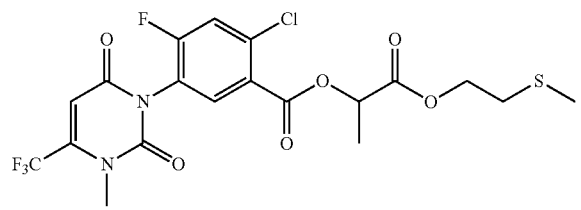

145.14 mg of 2-(methylthio)ethanol and 199.21 mg of triethylamine were added to a reaction flask, cooled in an ice bath, stirred, and blown with nitrogen, 3 mL of dichloromethane solution of the intermediate 156-3 (0.60 g) described in Example 23 was added dropwise, and then a reaction occurred at room temperature for 2 h. After the reaction was completed, column chromatography purification was carried out to obtain 409 mg of colorless oil as compound 190. $^1$H NMR (400 MHz, DMSO-d$_6$) δ 8.15 (d, J=7.8 Hz, 1H), 7.94 (d, J=9.6 Hz, 1H), 6.63 (d, J=2.9 Hz, 1H), 5.32 (dd, J=7.0, 2.0 Hz, 1H), 4.39-4.21 (m, 2H), 3.42 (s, 3H), 2.83-2.66 (m, 2H), 2.11-2.07 (m, 3H), 1.55 (d, J=7.0 Hz, 3H). LCMS (ESI) [M+H]$^+$=512.04, Found=512.54.

Example 28: Preparation of Compound 194

Step 1: Preparation of Compound 194

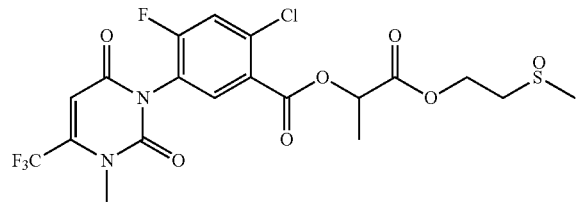

250.0 mg of compound 190 and 10 mL of dichloromethane were added to a reaction flask, cooled in an ice bath, stirred, and blown with nitrogen, 84.11 mg of m-chloroperoxybenzoic acid was added, and then a reaction occurred at room temperature for 2 h. After the reaction was completed, column chromatography purification was carried out to obtain 166 mg of colorless oil as compound 194. $^1$H NMR (400 MHz, DMSO-d$_6$) δ 8.21 (d, J=7.7 Hz, 1H), 8.01 (d, J=9.6 Hz, 1H), 6.70 (d, J=2.8 Hz, 1H), 5.41 (qt, J=7.2, 1.6 Hz, 1H), 4.70-4.43 (m, 2H), 3.48 (s, 3H), 3.27-3.00 (m, 2H), 2.65 (d, J=2.6 Hz, 3H), 1.61 (d, J=7.0 Hz, 3H). LCMS (ESI) [M+H]$^+$=529.04, Found=528.65.

Example 29: Preparation of Compound 195

Step 1: Preparation of Compound 195

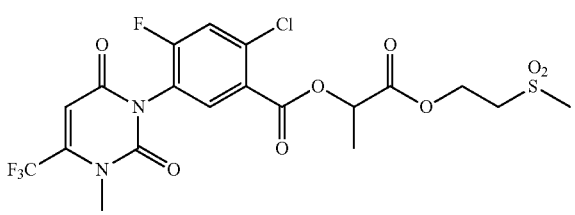

97.77 mg of 2-methylsulfonyl ethanol and 99.61 mg of triethylamine were added to a reaction flask, cooled in an ice bath, stirred, and blown with nitrogen, 2 mL of dichloromethane solution of the intel mediate 156-3 (0.30 g) described in Example 23 was added dropwise, and then a reaction occurred at room temperature for 2 h. After the reaction was completed; column chromatography purification was carried out to obtain 168 mg of compound 195, $^1$H NMR (400 MHz, DMSO-d$_6$) δ 8.16 (d, J=7.7 Hz, 1H), 7.94 (d, J=9.5 Hz, 1H), 6.63 (d, J=3.2 Hz, 1H), 5.43-5.32 (m, 1H), 4.57-4.41 (m, 2H), 3.55 (t, J=5.8 Hz, 2H), 3.02 (s, 3H), 1.54 (d, J=7.2 Hz, 3H). LCMS (ESI) [M+H]$^+$=545.03, Found=544.58.

Example 30: Preparation of Compound 198

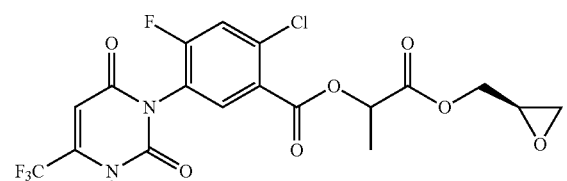

With reference to the methods of Examples 12 and 21, compound 198 was prepared by using the intermediate 156-3 described in Example 23 and (S)-glycidol. $^1$H NMR (400 MHz, CDCl$_3$) δ 7.97 (d, J=7.7 Hz, 1H), 7.40 (d, J=9.1 Hz, 1H), 6.38 (d, J=1.1 Hz, 1H), 5.37 (q, J=7.0 Hz, 1H), 4.49 (dd, J=12.2, 3.0 Hz, 1H), 4.07-3.94 (m, 1H), 3.57 (s, 3H), 3.22 (tt, J=9.8, 4.9 Hz, 1H), 2.84 (q, J=4.4 Hz, 1H), 2.63 (dd, J=4.7, 2.6 Hz, 1H), 1.62 (t, J=9.2 Hz, 3H). LCMS (ESI) [M+H]$^+$=495.05, Found=495.04.

Example 31: Preparation of Compound 199

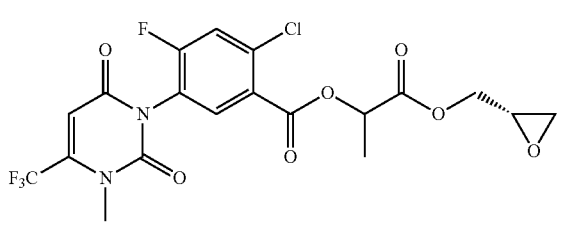 [SMILES: CC(OC(=O)c1cc(-n2c(=O)cc(C(F)(F)F)n(C)c2=O)c(F)cc1Cl)C(=O)OC[C@@H]1CO1]

With reference to the methods of Examples 13 and 22, compound 199 was prepared by using the intermediate 156-3 described in Example 23 and (R)-glycidol. $^1$H NMR (400 MHz, CDCl$_3$) δ 7.97 (d, J=7.7 Hz, 1H), 7.40 (d, J=9.2 Hz, 1H), 6.37 (d, J=2.3 Hz, 1H), 5.37 (qd, J=7.1, 2.2 Hz, 1H), 4.49 (dd, J=12.2, 2.2 Hz, 1H), 4.13-3.98 (m, 1H), 3.57 (d, J=2.0 Hz, 3H), 3.20 (tt, J=5.7, 2.8 Hz, 1H), 2.84 (t, J=4.5 Hz, 1H), 2.67 (dt, J=10.9, 5.6 Hz, 1H), 1.63 (d, J=7.1 Hz, 3H). LCMS (ESI) [M+H]$^+$=495.05, Found=495.20.

Example 32: Preparation of Compound 207

Step 1: Preparation of Intermediate 207-1

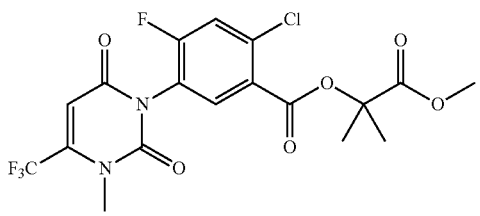 [SMILES: COC(=O)C(C)(C)OC(=O)c1cc(-n2c(=O)cc(C(F)(F)F)n(C)c2=O)c(F)cc1Cl]

2.36 g of methyl 2-hydroxyisobutyrate, 1.91 g of DMAP, and 50 g of dichloromethane were added to a reaction flask, blown with nitrogen, and stirred at room temperature. 5 g of the intermediate 1-8 described in Example 1 was added dropwise within 20 min, followed by stirring at room temperature for 1 h. After the reaction was completed, column chromatography purification was carried out to obtain 3.57 g of intermediate 207-1.

Step 2: Preparation of Intermediate 207-2

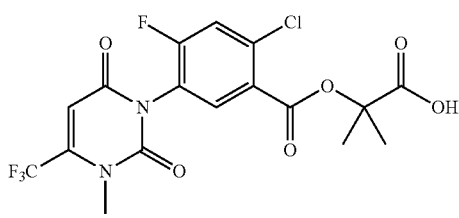 [SMILES: Cn1c(C(F)(F)F)cc(=O)n(-c2cc(C(=O)OC(C)(C)C(=O)O)c(Cl)cc2F)c1=O]

3.57 g of intermediate 207-1, 20 g of hydrochloric acid (36%), and 20 g of acetic acid were added into a reaction flask and stirred at 120° C. for 2 h. After a reaction ended, the reaction solution was poured into 100 ml of ice water, extraction was carried out with EA, and the organic phase was spun off to obtain 2.78 g of intermediate 207-2.

Step 3: Preparation of Compound 207-3

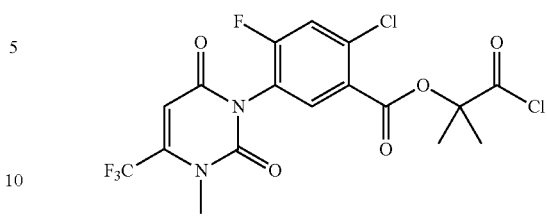

2.78 g of intermediate 207-2, 1.1 g of sulfoxide chloride, 30 g of 1,2-dichloroethane, and 2 drops of DMF were added into a reaction flask for reflux stirring at 90° C. After one hour of reaction, the solvent was spun off to obtain 3.2 g of intermediate 207-3.

Step 4: Preparation of Compound 207

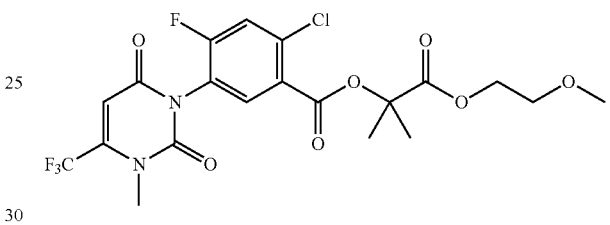

0.3 g of intermediate 207-3, 0.054 g of 2-methoxyethanol, 10 g of dichloromethane, and g of triethylamine were added into a reaction flask, blown with nitrogen, and stirred at room temperature. After the reaction was completed, 5 mL, of water was added, and the solution was stirred and separated to obtain an organic phase. The organic phase was dried, and the excess solvent was evaporated under reduced pressure. Column chromatography purification was carried out to obtain 120 mg of white solid as compound 207. $^1$H NMR (400 MHz, CDCl$_3$) δ 7.86 (d, J=7.7 Hz, 1H), 7.38 (d, J=9.2 Hz, 1H), 6.38 (s, 1H), 4.50-4.18 (m, 2H), 3.59 (s, 2H), 3.57 (s, 3H), 3.32 (s, 3H), 1.69 (s, 6H). LCMS (ESI) [M+H]$^+$=511.08, Found=511.12.

Example 33: Preparation of Compound 214

Step 1: Preparation of Compound 214

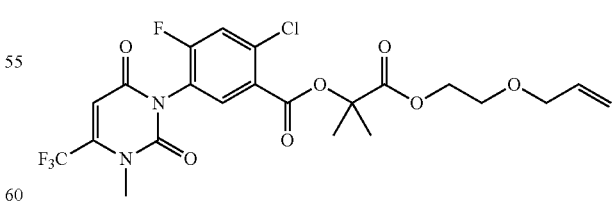

1.04 g of 2-allyloxyethanol, 1.24 g of DMAP, and 30 g of dichloromethane were added to a reaction flask, cooled in an ice bath, stirred, and blown with nitrogen, 20 mL of dichloromethane solution of the intermediate 207-3 (3.2 g) described in Example 32 was added dropwise, and then a reaction occurred at room temperature for 1 h. After the reaction was completed, column chromatography purification was carried out to obtain 600 mg of compound 214. ¹H NMR (400 MHz, DMSO-d₆) δ 8.07 (d, J=7.8 Hz, 1H), 7.92 (d, J=9.6 Hz, 1H), 6.63 (s, 1H), 5.90-5.73 (m, 1H), 5.25-5.08 (m, 2H), 4.27-4.19 (m, 2H), 3.91 (dt, J=5.3, 1.6 Hz, 2H), 3.59-3.55 (m, 2H), 3.42 (d, J=1.3 Hz, 3H), 1.63 (s, 6H). LCMS (ESI) [M+H]⁺=537.10, Found=536.98.

Example 34: Preparation of Compound 249

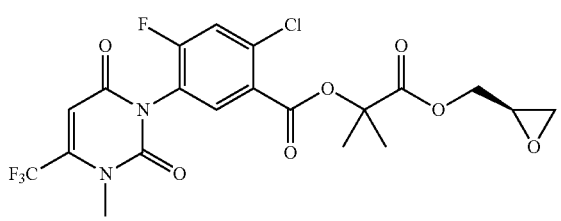 [SMILES: Cn1c(C(F)(F)F)cc(=O)n(-c2cc(C(=O)OC(C)(C)C(=O)OC[C@H]3CO3)c(Cl)cc2F)c1=O]

0.71 g of (S)-glycidol, 0.5 g of DMAP, 2 g of triethylamine, and 2 mL of dichloromethane were added to a reaction flask, cooled in an ice bath, and blown with nitrogen. 2.57 g of the intermediate 207-3 described in Example 32 was added dropwise to dissolve in 20 mL of dichloromethane solution, and a reaction occurred at room temperature for 3 h. After the reaction was completed, column chromatography purification was carried out to obtain 3 g of oily compound as compound 249. ¹H NMR (400 MHz, Chloroform-d) δ 7.87 (d, J=7.6 Hz, 1H), 7.39 (d, J=9.1 Hz, 1H), 6.38 (s, 1H), 4.45 (dd, J=12.2, 3.4 Hz, 1H), 4.04 (dd, J=12.2, 6.0 Hz, 1H), 3.57 (s, 3H), 3.21 (dq, J=6.4, 3.3 Hz, 1H), 2.83 (t, J=4.5 Hz, 1H), 2.64 (dd, J=4.9, 2.6 Hz, 1H), 1.70 (s, 6H). LCMS (ESI) [M+H]⁺=509.07, Found=508.93.

Example 35: Preparation of Compound 250

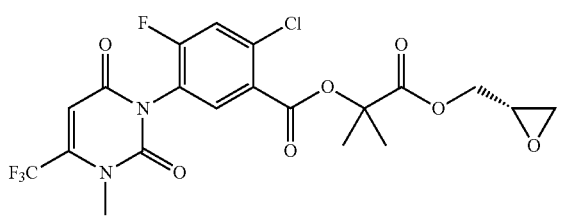 [SMILES: Cn1c(C(F)(F)F)cc(=O)n(-c2cc(C(=O)OC(C)(C)C(=O)OC[C@@H]3CO3)c(Cl)cc2F)c1=O]

0.71 g of (R)-glycidol, 0.5 g of DMAP, 2 g of triethylamine, and 2 mL of dichloromethane were added to a reaction flask, cooled in an ice bath, and blown with nitrogen. 20 mL of dichloromethane solution of 2.57 g of the intermediate 207-3 described in Example 32 was added dropwise, and a reaction occurred at room temperature for 3 h. After the reaction was completed, column chromatography purification was carried out to obtain 2.9 g of oily compound as compound 250. ¹H NMR (400 MHz, Chloroform-d) δ 7.87 (d, J=7.7 Hz, 1H), 7.39 (d, J=9.2 Hz, 1H), 6.38 (s, 1H), 4.44 (dd, J=12.2, 3.4 Hz, 1H), 4.04 (dd, J=12.2, 6.0 Hz, 1H), 3.56 (s, 3H), 3.20 (dq, J=6.1, 3.5 Hz, 1H), 2.82 (t, J=4.5 Hz, 1H), 2.63 (dd, J=4.8, 2.6 Hz, 1H), 1.70 (s, 6H). LCMS (ESI) [M+H]⁺=509.07, Found=509.10.

Example 36: Preparation of Compound 251

Step 1: Preparation of Compound 251

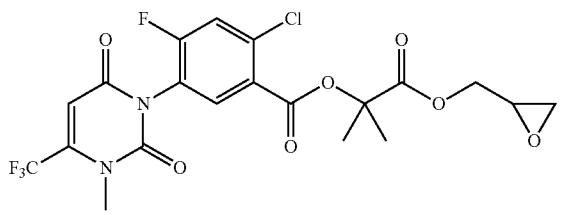 [SMILES: Cn1c(C(F)(F)F)cc(=O)n(-c2cc(C(=O)OC(C)(C)C(=O)OCC3CO3)c(Cl)cc2F)c1=O]

With reference to the methods of Examples 34 and 35, compound 251 was prepared by using the intermediate 207-3 described in Example 32 and glycidol. ¹H NMR (400 MHz, Chloroform-d) δ 7.87 (d, J=7.6 Hz, 1H), 7.39 (d, J=9.1 Hz, 1H), 6.38 (s, 1H), 4.45 (dd, J=12.2, 3.4 Hz, 1H), 4.04 (dd, J=12.2, 6.0 Hz, 1H), 3.57 (s, 3H), 3.21 (dq, J=6.4, 3.3 Hz, 1H), 2.83 (t, J=4.5 Hz, 1H), 2.64 (dd, J=4.9, 2.6 Hz, 1H), 1.70 (s, 6H). LCMS (ESI) [M+H]⁺=509.07, Found=508.97.

Example 37: Preparation of Compound 258

Step 1: Preparation of Compound 258-1

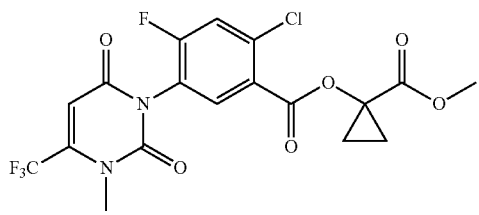

0.6 g of methyl 1-hydroxy-1-cyclopropanecarboxylate, 0.57 g of DMAP, and 25 g of dichloromethane were added to a reaction flask, cooled in an ice bath, stirred, and blown with nitrogen, 10 mL of dichloromethane solution of the intermediate 1-8 (1.22 g) described in Example 1 was added dropwise, and then a reaction occurred at room temperature for 1 h. After the reaction was completed, column chromatography purification was carried out to obtain 1.1 g of intermediate 258-1.

Step 2: Preparation of Compound 258-2

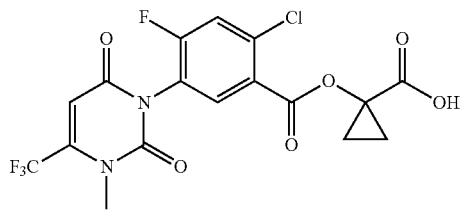 [SMILES: Cn1c(C(F)(F)F)cc(=O)n(-c2cc(C(=O)OC3(C(=O)O)CC3)c(Cl)cc2F)c1=O]

1.1 g of intermediate 258-1, 8 g of hydrochloric acid (36%), and 8 g of acetic acid were added into a reaction flask and stirred at 110° C. for 4 h. After a reaction ended, the reaction solution was poured into 100 ml of ice water, extraction was carried out with EA, and the organic phase was spun off to obtain 1.06 g of intermediate 258-2.

Step 3: Preparation of Compound 258-3

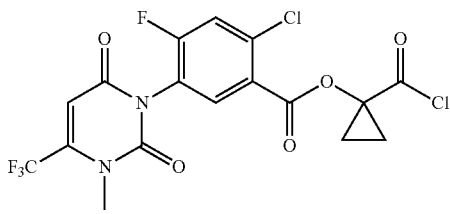

1.06 g of intermediate 258-2, 0.42 g of sulfoxide chloride, 20 g of 1,2-dichloroethane, and 2 drops of DMF were added into a reaction flask for reflux stirring at 90° C. After one hour of reaction, the solvent was spun off to obtain 1.1 g of intermediate 258-3.

Step 4: Preparation of Compound 258

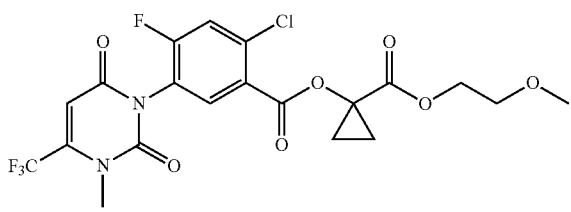 [SMILES: COCCOC(=O)C1(OC(=O)c2cc(-n3c(=O)cc(C(F)(F)F)n(C)c3=O)c(F)cc2Cl)CC1]

0.211 g of 2-methoxyethanol, 0.323 g of triethylamine, and 15 g of dichloromethane were added to a reaction flask, cooled in an ice bath, stirred, and blown with nitrogen, 10 mL of di chloromethane solution of the intermediate 258-3 (1.0 g) was added dropwise, and then a reaction occurred at room temperature for 1 h. After the reaction was completed, column chromatography purification was carried out to obtain 201 mg of compound 258. $^1$H NMR (400 MHz, DMSO-$d_6$) δ 8.21 (d, J=7.6 Hz, 1H), 8.01 (d, J=9.4 Hz, 1H), 6.70 (s, 1H), 4.29 (t, J=4.7 Hz, 2H), 3.57 (t, J=4.6 Hz, 2H), 3.49 (s, 3H), 3.29 (s, 3H), 1.67-1.48 (m, 4H). LCMS (ESI) [M+H]$^+$=509.07, Found=508.92.

Example 38: Preparation of Compound 300

Step 1: Preparation of Compound 300

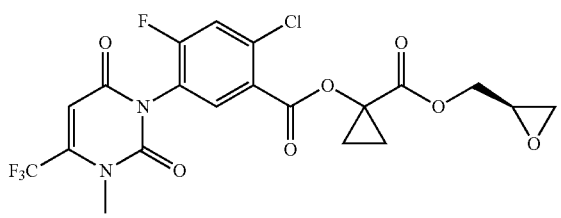 [SMILES: Cn1c(C(F)(F)F)cc(=O)n(-c2cc(C(=O)OC3(C(=O)OC[C@H]4CO4)CC3)c(Cl)cc2F)c1=O]

0.308 g of (S)-glycidol, 0.485 g of triethylamine, and 20 g of dichloromethane were added to a reaction flask, cooled in an ice bath, stirred, and blown with nitrogen, 15 mL of dichloromethane solution of the intermediate 258-3 (1.5 g) described in Example 37 was added dropwise, and then a reaction occurred at room temperature for 1 h. After the reaction was completed, column chromatography purification was carried out to obtain 212 mg of compound 300. $^1$H NMR (400 MHz, DMSO-$d_6$) δ 8.22 (d, J=7.8 Hz, 1H), 8.01 (d, J=9.6 Hz, 1H), 6.69 (s, 1H), 4.52 (dd, J=12.3, 2.6 Hz, 1H), 4.03 (dd, J=12.3, 6.3 Hz, 1H), 3.51-3.45 (m, 3H), 3.24 (ddt, J=6.7, 4.2, 2.6 Hz, 1H), 2.83 (dd, J=5.0, 4.2 Hz, 1H), 2.68 (dd, J=5.0, 2.6 Hz, 1H), 1.68-1.51 (m, 4H). LCMS (ESI) [M+H]$^+$=507.05, Found=506.96.

Example 39: Preparation of Compound 301

Step 1: Preparation of Compound 301

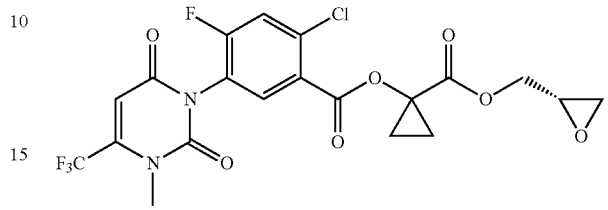

0.205 g of (R)-glycidol, 0.323 g of triethylamine, and 15 g of dichloromethane were added to a reaction flask, cooled in an ice bath, stirred, and blown with nitrogen, 15 mL of dichloromethane solution of the intermediate 258-3 (1.0 g) descried in Example 37 was added dropwise, and then a reaction occurred at room temperature for 1 h. After the reaction was completed, column chromatography purification was carried out to obtain 222 mg of compound 301. $^1$H NMR (400 MHz, DMSO-$d_6$) δ 8.15 (d, J=7.8 Hz, 1H), 7.94 (d, J=9.6 Hz, 1H), 6.63 (s, 1H), 4.46 (dd, J=12.3, 2.7 Hz, 1H), 3.97 (dd, J=12.3, 6.2 Hz, 1H), 3.46-3.40 (m, 3H), 3.18 (ddt, J=6.7, 4.2, 2.6 Hz, 1H), 2.77 (dd, J=5.0, 4.3 Hz, 1H), 2.62 (dd, J=5.0, 2.6 Hz, 1H), 1.61-1.45 (m, 4H). LCMS (ESI) [M+H]$^+$=507.05, Found=507.10.

Example 40: Preparation of Compound 302

Step 1: Preparation of Compound 302

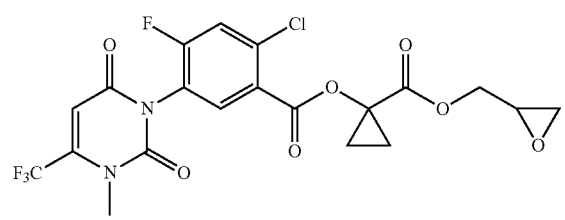 [SMILES: Cn1c(C(F)(F)F)cc(=O)n(-c2cc(C(=O)OC3(C(=O)OCC4CO4)CC3)c(Cl)cc2F)c1=O]

With reference to the methods of Examples 38 and 39, compound 302 was prepared by using the intermediate 258-3 described in Example 37 and glycidol. $^1$H NMR (400 MHz, DMSO-$d_6$) δ 8.22 (d, J=7.8 Hz, 1H), 8.01 (d, J=9.6 Hz, 1H), 6.69 (s, 1H), 4.52 (dd, J=12.3, 2.6 Hz, 1H), 4.03 (dd, J=12.3, 6.3 Hz, 1H), 3.51-3.45 (m, 3H), 3.24 (ddt, J=6.7, 4.2, 2.6 Hz, 1H), 2.83 (dd, J=5.0, 4.2 Hz, 1H), 2.68 (dd, J=5.0, 2.6 Hz, 1H), 1.68-1.51 (m, 4H). LCMS (ESI) [M+H]$^+$=507.05, Found=506.88.

Example 41: Greenhouse Experiments

A herbicidal activity test method for the compounds of the present invention was as follows:

Seed Treatment; pre-emergence: quantitative seeds of gramineous weeds (*Echinochloa crusgalli, Eleusine indica, Digitaria sanguinalis, Alopecurus japonicus, Beckmannia syzigachne, Leptochloa chinensis, Polypogon fugax, Alopecurus, aequalis, Lolium multiflorum,* and *Poa annua*), broad-leaved weeds (*Eclipta prostrata, Amaranthus retro-* flexus, Brassica juncea, Malachium aquaticum, Conyza canadensis, and Sesbania cannabina), and Cyperus iria were sown in plastic pots having a diameter of 7 cm and holes at the bottom and filled with nutrient soil (sandy soil, pH 6.1, organic matter 1%) respectively, the seeds were covered with an appropriate amount of soil after being sown, then the soil was wetted with water from the bottom, the seeds were cultured in a constant-temperature illuminated culture room for 24 h, and the soil was sprayed by using a 3WP-2000 traveling spray tower produced by the Nanjing Institute of Agricultural Mechanization of the Ministry of Agriculture, where a rotational speed of a main shaft was 96 mm/r, a spray height was 300 mm, an effective spraying range of a nozzle was 350 mm, a spray area was 0.35 m 2, and a flow rate at the nozzle was 390 mL/min.

Post-emergence: an appropriate quantity of seeds of gramineous weeds (Echinochloa crusgalli, Eleusine indica, Digitaria sanguinalis, Alopecurus japonicus, Beckmannia syzigachne, Leptochloa chinensis, Polypogon fugax, Alopecurus aequalis, Lolium multiflorum, and Poa annua), broad-leaved weeds (Eclipta prostrata, Amaranthus retroflexus, Brassica juncea, Malachium aquaticum, Conyza canadensis, and Sesbania cannabina), and Cyperus iria were sown in plastic pots having a diameter of 7 cm and holes at the bottom and filled with nutrient soil (sandy soil, pH 6.1, organic matter 1%) respectively, the seeds were covered with an appropriate amount of soil after being sown, then the soil was wetted with water from the bottom, the seeds were cultured in a constant-temperature illuminated culture room until a 2-4 leaf stage, and stems and leaves underwent spray treatment. After the treatment, the test materials were placed in a laboratory and cultured in the constant-temperature illuminated culture room after the liquid was naturally dry in the shade, and results were determined 21 days later.

Classification standards for prevention and control effects:

A indicates that the inhibition rate was greater than or equal to 85% to 100%;
B indicates that the inhibition rate was greater than or equal to 70% to less than 85%;
C indicates that the inhibition rate was greater than or equal to 55% to less than 70%;
D indicates that the inhibition rate was less than 55%.

The test results showed that the compounds of the general formula (I) generally had excellent prevention and control effects on various weeds at a dose of 30 g a.i./hm², reaching class A.

According to the foregoing test method, a parallel experiment was carried out on herbicidal activities of some compounds of the general formula (I), the compound Butafenacil (compound 47 in the patent specification) specifically disclosed in U.S. Pat. No. 5,183,492A, and the compound CK (compound 1 in the patent specification) specifically disclosed in U.S. Pat. No. 5,183,492A, at application doses of 7.5 g a.i./ha and 15 g a.i./ha. Results were shown in Table 2:

TABLE 2

Herbicidal activities of some compounds of the general formula (I) and control compounds (post-emergence, fresh weight inhibition rate %)

| Number of compound | Dose a.i./ha | Alopecurus japonicus | Polypogon fugax | Sesbania cannabina |
|---|---|---|---|---|
| 3 | 7.5 | B | B | A |
|  | 15 | A | A | A |
| 105 | 7.5 | A | B | A |
|  | 15 | A | A | A |

TABLE 2-continued

Herbicidal activities of some compounds of the general formula (I) and control compounds (post-emergence, fresh weight inhibition rate %)

| Number of compound | Dose a.i./ha | Alopecurus japonicus | Polypogon fugax | Sesbania cannabina |
|---|---|---|---|---|
| 207 | 7.5 | A | A | A |
|  | 15 | A | A | A |
| 214 | 7.5 | A | A | A |
|  | 15 | A | A | A |
| 258 | 7.5 | A | A | A |
|  | 15 | A | A | A |
| Butafenacil | 7.5 | D | D | C |
|  | 15 | D | C | B |
| CK | 7.5 | D | D | C |
|  | 15 | C | C | B |

Described above are preferred embodiments of the present invention. It should be noted that, for those of ordinary skill in the art, many variations and improvements may be made without departing from the conception of the present invention, and the variations and improvements fall into the protection scope of the present invention.

What is claimed is:

1. A uracil compound containing a carboxylate fragment, a structure of the uracil compound containing the carboxylate fragment is shown hi a formula (I):

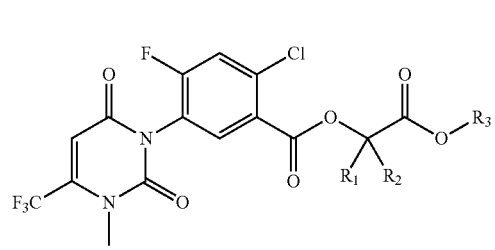

in the formula (I):
R₁ and R₂ are each selected from hydrogen or methyl; or the R₁, the R₂, and a carbon atom attached to the R₁ and the R₂ form a 3-membered carbocycle;
R₃ is selected from $C_{1-3}$ alkoxy $C_{1-3}$ alkyl, $C_{1-3}$ haloalkoxy $C_{1-3}$ alkyl, $C_{2-6}$ alkenoxy $C_{1-3}$ alkyl, $C_{2-6}$ haloalkenoxy $C_{1-3}$ alkyl, $C_{2-6}$ alkynoxy $C_{1-3}$ alkyl, $C_{2-6}$ haloalkynoxy $C_{1-3}$ alkyl, $C_{1-3}$ alkyl $S(O)_n$ $C_{1-3}$ alkyl, $C_{3-6}$ oxygen-containing cycloalkyl $C_{1-3}$ alkyl, or $C_{3-9}$ oxygen-containing cycloalkyl;
n=0, 1, or 2; and
when the R₁ is hydrogen and the R₂ is methyl, a chiral carbon atom connected to the R₁ and the R₂ is selected from either an R configuration or an S configuration, or a mixture of the R configuration and the S configuration; and in the mixture, a ratio of the R configuration to the S configuration is 1:99 to 99:1.

2. The uracil compound containing the carboxylate fragment according to claim 1, wherein
R₃ is selected from the $C_{1-3}$ alkoxy $C_{1-3}$ alkyl, the $C_{1-3}$ haloalkoxy $C_{1-3}$ alkyl, the $C_{2-6}$ alkenoxy $C_{1-3}$ alkyl, the $C_{2-6}$ haloalkenoxy $C_{1-3}$ alkyl, the $C_{2-6}$ alkynoxy $C_{1-3}$ alkyl, the $C_{2-6}$ haloalkynoxy $C_{1-3}$ alkyl, the $C_{3-6}$ oxygen-containing cycloalkyl $C_{1-3}$ alkyl, or the $C_{3-9}$ oxygen-containing cycloalkyl.

3. The uracil compound containing the carboxylate fragment according to claim 1, wherein
R₁ and R₂ are each selected from hydrogen or methyl; and
R₃ is selected from the $C_{1-3}$ alkoxy $C_{1-3}$ alkyl, the $C_{1-3}$ haloalkoxy $C_{1-3}$ alkyl, the $C_{2-6}$ alkenoxy $C_{1-3}$ alkyl, the $C_{2-6}$ haloalkenoxy $C_{1-3}$ alkyl, the $C_{2-6}$ alkynoxy $C_{1-3}$ alkyl, the $C_{2-6}$ haloalkynoxy $C_{1-3}$ alkyl, the $C_{3-6}$ oxygen-containing cycloalkyl $C_{1-3}$ alkyl, or the $C_{3-9}$ oxygen-containing cycloalkyl.

4. A composition, comprising the uracil compound containing the carboxylate fragment according to claim 1 as an active ingredient, wherein a weight percentage content of the active ingredient in the composition is 0.1-99.9%.

5. The composition according to claim 4, wherein $R_3$ is selected from the $C_{1-3}$ alkoxy $C_{1-3}$ alkyl, the $C_{1-3}$ haloalkoxy $C_{1-3}$ alkyl, the $C_{2-6}$ alkenoxy $C_{1-3}$ alkyl, the $C_{2-6}$ haloalkenoxy $C_{1-3}$ alkyl, the $C_{2-6}$ alkynoxy $C_{1-3}$ alkyl, the $C_{2-6}$ haloalkynoxy $C_{1-3}$ alkyl, the $C_{3-6}$ oxygen-containing cycloalkyl $C_{1-3}$ alkyl, or the $C_{3-9}$ oxygen-containing cycloalkyl.

6. The composition according to claim 4, wherein
$R_1$ and $R_2$ are selected from hydrogen or methyl respectively; and
$R_3$ is selected from the $C_{1-3}$ alkoxy $C_{1-3}$ alkyl, the $C_{1-3}$ haloalkoxy $C_{1-3}$ alkyl, the $C_{2-6}$ alkenoxy $C_{1-3}$ alkyl, the $C_{2-6}$ haloalkenoxy $C_{1-3}$ alkyl, the $C_{2-6}$ alkynoxy $C_{1-3}$ alkyl, the $C_{2-6}$ haloalkynoxy $C_{1-3}$ alkyl, the $C_{3-6}$ oxygen-containing cycloalkyl $C_{1-3}$ alkyl, or the $C_{3-9}$ oxygen-containing cycloalkyl.

7. A method for preparing a uracil compound containing a carboxylate fragment, a structure of the uracil compound containing the carboxylate fragment is shown in a formula (I):

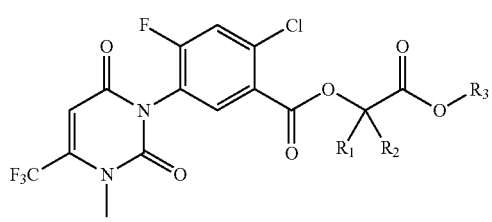

wherein the method comprises a contact reaction between a carboxylic acid compound shown in a formula (II) and different substituted alcohol, halogenated, or sulfonate compounds in a presence of a solvent,

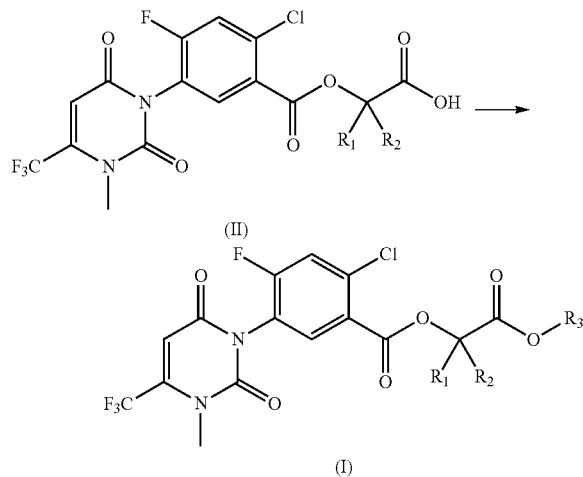

wherein in the general formulas (I) and (II):
$R_1$ and $R_2$ are each selected from hydrogen or methyl; or the $R_1$, the $R_2$, and a carbon atom attached to the $R_1$ and the $R_2$ form a 3-membered carbocycle;

$R_3$ is selected from $C_{1-3}$ alkoxy $C_{1-3}$ alkyl, $C_{1-3}$ haloalkoxy $C_{1-3}$ alkyl, $C_{2-6}$ alkenoxy $C_{1-3}$ alkyl, $C_{2-6}$ haloalkenoxy $C_{1-3}$ alkyl, $C_{2-6}$ alkynoxy $C_{1-3}$ alkyl, $C_{2-6}$ haloalkynoxy $C_{1-3}$ alkyl, $C_{1-3}$ alkyl $S(O)_n$ $C_{1-3}$ alkyl, $C_{3-6}$ oxygen-containing cycloalkyl $C_{1-3}$ alkyl, or $C_{3-9}$ oxygen-containing cycloalkyl;
n=0, 1, or 2; and
when the $R_1$ is hydrogen and the $R_2$ is methyl, a chiral carbon atom connected to the $R_1$ and the $R_2$ is selected from either an R configuration or an S configuration, or a mixture of the R configuration and the S configuration; and in the mixture, a ratio of the R configuration to the S configuration is 1:99 to 99:1.

8. The method according to claim 7, wherein a reaction temperature is 0-160° C.

9. The method according to claim 7, wherein a reaction time is 2-15 h.

10. The method according to claim 7, wherein the solvent is selected from at least one of dichloromethane, 1,2-dichloroethane, tetrahydrofuran, acetonitrile, 1,4-dioxane, toluene, o-xylene, m-xylene, p-xylene, n-heptane, n-octane, and n-nonane.

11. The method according to claim 7, wherein a molar ratio of the carboxylic acid compound shown in the formula (II) to the different substituted alcohol, halogenated, or sulfonate compounds is 1:(1-4).

12. The method according to claim 7, wherein
$R_3$ is selected from the $C_{1-3}$ alkoxy $C_{1-3}$ alkyl, the $C_{1-3}$ haloalkoxy $C_{1-3}$ alkyl, the $C_{2-6}$ alkenoxy $C_{1-3}$ alkyl, the $C_{2-6}$ haloalkenoxy $C_{1-3}$ alkyl, the $C_{2-6}$ alkynoxy $C_{1-3}$ alkyl, the $C_{2-6}$ haloalkynoxy $C_{1-3}$ alkyl, the $C_{3-6}$ oxygen-containing cycloalkyl $C_{1-3}$ alkyl, or the $C_{3-9}$ oxygen-containing cycloalkyl.

13. The method according to claim 7, wherein
$R_1$ and $R_2$ are each selected from hydrogen or methyl; and
$R_3$ is selected from the $C_{1-3}$ alkoxy $C_{1-3}$ alkyl, the $C_{1-3}$ haloalkoxy $C_{1-3}$ alkyl, the $C_{2-6}$ alkenoxy $C_{1-3}$ alkyl, the $C_{2-6}$ haloalkenoxy $C_{1-3}$ alkyl, the $C_{2-6}$ alkynoxy $C_{1-3}$ alkyl, the $C_{2-6}$ haloalkynoxy $C_{1-3}$ alkyl, the $C_{3-6}$ oxygen-containing cycloalkyl $C_{1-3}$ alkyl, or the $C_{3-9}$ oxygen-containing cycloalkyl.

14. A method of using a uracil compound containing a carboxylate fragment, a structure of the uracil compound containing the carboxylate fragment is shown in formula (I):

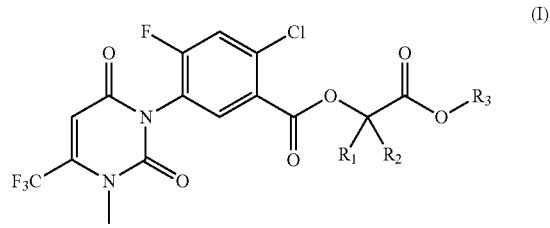

in the formula (I):
$R_1$ and $R_2$ are each selected from hydrogen or methyl; or the $R_1$ the $R_2$, and a carbon atom attached to the $R_1$ and the $R_2$ form a 3-membered carbocycle;
$R_3$ is selected from $C_{1-3}$ alkoxy $C_{1-3}$ alkyl, $C_{1-3}$ haloalkoxy $C_{1-3}$ alkyl, $C_{2-6}$ alkenoxy $C_{1-3}$ alkyl, $C_{2-6}$ haloalkenoxy $C_{1-3}$ alkyl, $C_{2-6}$ alkynoxy $C_{1-3}$ alkyl, $C_{2-6}$ haloalkynoxy $C_{1-3}$ alkyl, $C_{1-3}$ alkyl $S(O)_n$ $C_{1-3}$ alkyl, $C_{3-6}$ oxygen-containing cycloalkyl $C_{1-3}$ alkyl, or $C_{3-9}$ oxygen-containing cycloalkyl;
n=0, 1, or 2; and when the $R_1$ is hydrogen and the $R_2$ is methyl, a chiral carbon atom connected to the $R_1$ and the $R_2$ is selected from either an R configuration or an S configuration, or a mixture of the R configuration and the S configuration; and in the mixture, a ratio of the R configuration to the S configuration is 1:99 to 99:1 in prevention and control of weeds, comprising a step of:

treating seeds pre-emergence with the uracil compound or treating plants post-emergence with the uracil compound.

15. The method according to claim 14, wherein $R_3$ is selected from the $C_{1-3}$ alkoxy $C_{1-3}$ alkyl, the $C_{1-3}$ haloalkoxy $C_{1-3}$ alkyl, the $C_{2-6}$ alkenoxy $C_{1-3}$ alkyl, the $C_{2-6}$ haloalkenoxy $C_{1-3}$ alkyl, the $C_{2-6}$ alkynoxy $C_{1-3}$ alkyl, the $C_{2-6}$ haloalkynoxy $C_{1-3}$ alkyl, the $C_{3-6}$ oxygen-containing cycloalkyl $C_{1-3}$ alkyl, or the $C_{3-9}$ oxygen-containing cycloalkyl.

16. The method according to claim 14, wherein $R_1$ and $R_2$ are each selected from the hydrogen or the methyl; and $R_3$ is selected from the $C_{1-3}$ alkoxy $C_{1-3}$ alkyl, the $C_{1-3}$ haloalkoxy $C_{1-3}$ alkyl, the $C_{2-6}$ alkenoxy $C_{1-3}$ alkyl, the $C_{2-6}$ haloalkenoxy $C_{1-3}$ alkyl, the $C_{2-6}$ alkynoxy $C_{1-3}$ alkyl, the $C_{2-6}$ haloalkynoxy $C_{1-3}$ alkyl, the $C_{3-6}$ oxygen-containing cycloalkyl $C_{1-3}$ alkyl, or the $C_{3-9}$ oxygen-containing cycloalkyl.

* * * * *